(12) United States Patent
Lachenbruch et al.

(10) Patent No.: US 10,010,446 B2
(45) Date of Patent: Jul. 3, 2018

(54) COOLING SYSTEM FOR AN OCCUPANT OF AN OCCUPANT SUPPORT AND A COOLING GARMENT

(75) Inventors: Charles A Lachenbruch, Lakeway, TX (US); Andrew Kerr, Harrison, OH (US); Christopher R O'Keefe, Batesville, IN (US); Timothy J Receveur, Guilford, IN (US); Rachel Williamson, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 2236 days.

(21) Appl. No.: 12/984,976

(22) Filed: Jan. 5, 2011

(65) Prior Publication Data

US 2012/0172959 A1 Jul. 5, 2012

(51) Int. Cl.
*A61F 7/00* (2006.01)
*A41D 19/00* (2006.01)
(Continued)

(52) U.S. Cl.
CPC ........ *A61F 7/0085* (2013.01); *A41D 19/0037* (2013.01); *A41D 13/0053* (2013.01);
(Continued)

(58) Field of Classification Search
CPC .. A61F 7/0053; A61F 2007/006; A47C 21/04; A47C 21/044; A47C 21/048
(Continued)

(56) References Cited

U.S. PATENT DOCUMENTS 2,113,253 A * 4/1938 Gray ................................ 601/9
2,527,039 A * 10/1950 Swanson ......................... 607/83
(Continued)

FOREIGN PATENT DOCUMENTS

EP 1009342 B1 10/2004
WO 2004/092658 A1 10/2004

OTHER PUBLICATIONS

"Inhibition of shivering in man by thermal stimulation of the facial area", Authors: I.B. Mekjavic and O. Eiken. Department of Kinesiology, Simon Fraser University, Burnaby, Canada, and Department of Environmental Medicine, Karolinska Institute, Stockholm, Sweden. Acta Physiol Scand 1985, 125, 633-637.
(Continued)

*Primary Examiner* — Kaitlyn Smith
(74) *Attorney, Agent, or Firm* — Kenneth C. Baran

(57) ABSTRACT

A cooling system for an occupant of an occupant support comprises a coolant conduit having an inlet for receiving coolant and an outlet for discharging the coolant to a destination. The conduit is nonpermanently and manually shape adjustable, shape stable subsequent to adjustment, and removably securable to the occupant support, the occupant or both. In one embodiment the destination is an ambient environment selected to achieve targeted coolant delivery to a localized region of the occupant's body. A cooling glove to be worn by a user has at least one coolant intake and at least one of a) a coolant passage extending from the coolant intake to an exhaust opening which exhausts coolant to an ambient environment; and
b) a cooperative relationship with the user which defines a fluid pathway bounded in part by the glove and in part by the user and which discharges coolant to an ambient environment.

8 Claims, 22 Drawing Sheets

(51) Int. Cl.
 *A41D 13/005* (2006.01)
 *A41D 19/015* (2006.01)
(52) U.S. Cl.
 CPC ............................ *A41D 19/01541* (2013.01); *A61F 2007/0002* (2013.01); *A61F 2007/0036* (2013.01); *A61F 2007/0064* (2013.01)
(58) Field of Classification Search
 USPC .............................. 5/421, 423, 600; 607/107
 See application file for complete search history.

(56) References Cited

U.S. PATENT DOCUMENTS

| | | | |
|---|---|---|---|
| 2,600,240 A * | 6/1952 | Grieb .............................. | 600/22 |
| 2,648,327 A * | 8/1953 | Gibbon .......................... | 600/22 |
| 2,881,758 A * | 4/1959 | Motsinger ................ | 128/201.25 |
| 2,933,082 A * | 4/1960 | Billin ........................... | 600/531 |
| 3,230,556 A | 1/1966 | Wiusor | |
| 3,335,713 A * | 8/1967 | Grosholz et al. ............... | 600/22 |
| 3,468,299 A * | 9/1969 | Amato ......................... | 126/204 |
| 3,477,071 A * | 11/1969 | Emerson ........................... | 5/609 |
| 3,477,072 A * | 11/1969 | Frost ................................ | 5/710 |
| 3,757,366 A * | 9/1973 | Sacher ............................. | 5/423 |
| 3,866,612 A * | 2/1975 | Buker ........................... | 607/107 |
| 4,706,658 A | 11/1987 | Cronin | |
| 4,787,104 A * | 11/1988 | Grantham ........................ | 5/613 |
| 5,000,164 A * | 3/1991 | Cooper ........................... | 601/11 |
| 5,062,424 A * | 11/1991 | Hooker ......................... | 128/897 |
| 5,507,792 A * | 4/1996 | Mason et al. ................ | 607/104 |
| 5,539,943 A * | 7/1996 | Romano ........................ | 5/655.5 |
| 5,606,756 A * | 3/1997 | Price ............................... | 5/713 |
| 6,141,806 A * | 11/2000 | Bobey et al. .................... | 5/600 |
| 6,245,094 B1 * | 6/2001 | Pompei .......................... | 607/104 |
| 6,487,871 B1 | 12/2002 | Augustine et al. | |
| 6,497,720 B1 * | 12/2002 | Augustine et al. ............. | 607/96 |
| 6,581,400 B2 | 6/2003 | Augustine et al. | |
| 6,641,601 B1 | 11/2003 | Augustine et al. | |
| 6,689,155 B2 * | 2/2004 | Gammons et al. ........... | 607/109 |
| 6,730,115 B1 * | 5/2004 | Heaton ......................... | 607/104 |
| 6,800,087 B2 * | 10/2004 | Papay et al. ................... | 607/104 |
| 6,827,729 B2 * | 12/2004 | Gammons et al. ........... | 607/109 |
| 7,014,431 B2 | 3/2006 | Hansen et al. | |
| 7,022,130 B2 * | 4/2006 | Gammons et al. ........... | 607/109 |
| 7,137,992 B2 * | 11/2006 | Zhang ........................... | 607/110 |
| 7,226,454 B2 | 6/2007 | Albrecht et al. | |
| 7,364,584 B2 | 4/2008 | Anderson | |
| 7,470,280 B2 | 12/2008 | Bieberich | |
| 7,497,870 B2 * | 3/2009 | Frey et al. ..................... | 607/107 |
| 7,520,889 B2 | 4/2009 | Van Duren | |
| 7,555,792 B2 * | 7/2009 | Heaton et al. ..................... | 5/423 |
| 7,572,285 B2 * | 8/2009 | Frey et al. ..................... | 607/104 |
| 7,749,261 B2 | 7/2010 | Hansen et al. | |
| 7,818,835 B2 * | 10/2010 | Heaton et al. ..................... | 5/423 |
| 7,914,565 B2 * | 3/2011 | Leason et al. ................ | 607/107 |
| 7,937,789 B2 * | 5/2011 | Feher .............................. | 5/423 |
| 8,327,477 B2 * | 12/2012 | Lachenbruch et al. ........... | 5/421 |
| 8,353,069 B1 * | 1/2013 | Miller .............................. | 5/423 |
| 8,578,527 B2 * | 11/2013 | Lachenbruch et al. ........... | 5/421 |
| 2002/0103520 A1 | 8/2002 | Latham | |
| 2003/0014817 A1 * | 1/2003 | Gallant et al. ..................... | 5/600 |
| 2003/0023292 A1 * | 1/2003 | Gammons et al. ........... | 607/109 |
| 2003/0140418 A1 * | 7/2003 | Klamm ............................. | 5/423 |
| 2003/0188387 A1 * | 10/2003 | Leventhal et al. ................ | 5/660 |
| 2004/0030373 A1 * | 2/2004 | Ellingboe et al. ............ | 607/104 |
| 2004/0064170 A1 | 4/2004 | Radons | |
| 2004/0168459 A1 | 9/2004 | Blackstone | |
| 2004/0220649 A1 * | 11/2004 | Gammons et al. ........... | 607/109 |
| 2005/0114981 A1 | 6/2005 | Shim | |
| 2005/0172655 A1 | 8/2005 | Naaman | |
| 2005/0283913 A1 | 12/2005 | Heaton | |
| 2006/0026743 A1 | 2/2006 | Farnworth | |
| 2006/0053554 A1 | 3/2006 | Acton | |
| 2006/0212102 A1 * | 9/2006 | Frey et al. ..................... | 607/104 |
| 2006/0235497 A1 * | 10/2006 | Zanotti ......................... | 607/104 |
| 2007/0093883 A1 | 4/2007 | Anderson et al. | |
| 2007/0093884 A1 | 4/2007 | Anderson et al. | |
| 2008/0077033 A1 * | 3/2008 | Figueiredo et al. .......... | 600/529 |
| 2009/0062891 A1 | 3/2009 | Bieberich | |
| 2009/0143844 A1 * | 6/2009 | Cazzini ......................... | 607/104 |
| 2009/0216304 A1 * | 8/2009 | Heaton K et al. ............ | 607/104 |
| 2009/0312676 A1 * | 12/2009 | Rousso et al. ................. | 601/15 |
| 2010/0125928 A1 | 5/2010 | Smith | |
| 2010/0205739 A1 * | 8/2010 | Gallant et al. .................... | 5/600 |
| 2011/0172749 A1 * | 7/2011 | Christensen et al. ......... | 607/104 |
| 2011/0202019 A1 * | 8/2011 | Cooper et al. ................ | 604/291 |
| 2011/0289684 A1 * | 12/2011 | Parish et al. ...................... | 5/421 |
| 2012/0065716 A1 * | 3/2012 | Gill et al. ..................... | 607/107 |
| 2013/0103127 A1 * | 4/2013 | Muller et al. ................. | 607/107 |
| 2013/0152923 A1 * | 6/2013 | Andrieux et al. ........ | 128/202.22 |

OTHER PUBLICATIONS

"Importance of skin temperature in the regulation of sweating", Authors: Ethan R. Nadel, Robert W. Bullard and J.A.J. Stolwijk. John B. Pierce Foundation Laboratory and Department of Epidemiology, Yale University School of Medicine, New Haven, Connecticut 06519. Journal of Applied Physiology vol. 31, No. 1, Jul. 1971. Printed in U.S.A.

"Increasing Mean Skin Temperature Linearly Reduces the Core-temperature Thresholds for Vasoconstriction and Shivering in Humans", Authors: Christy Cheng, M.D., Takashi Matsukawa, M.D., Daniel I. Sessler, M.D., Makoto Ozaki, M.D., Andrea Kurz, M.D., Benjamin Merrifield, B.A., Hank Lin, B.A., Par Olofsson, B.A. Anesthesiology 82:1160-1168, 1995 © 1995 American Society of Anesthesiologists, Inc. J.B. Lippincott Company, Philadelphia.

"Control of Local and Total Sweating During Exercise Transients", Authors: E.R. Nadel, J.W. Mitchell and J.A.J. Stolwijk. Int. J. Biometeor. 1971, vol. 15, No. 2-4, pp. 201-206.

"Palm cooling to reduce heat strain in subjects during simulated armoured vehicle transport", Authors: Matthew R. Kuennen, Trevor L. Gillum, Fabiano T. Amorim, Young Sub Kwon, and Suzanne M. Schneider. Exercise Physiology Laboratory, Department of Health, Exercise and Sports Sciences, University of New Mexico, MSC 04 2610, Albuquerque, NM 87131-0001, USA. Universidade Federal dos Vales do Jequitinhonha e Mucuri (UFVJM), Rua da Gloria, n187 Centro, Diamantina CEP 39100-000, Brazil. Accepted: Dec. 9, 2009/Published Online: Dec. 24, 2009.

Letter to European Patent Office sent Jan. 8, 2013, Response to Rule 69 EPC, From Alice Findlay, European Patent Attorney, Reddie & Grose, European Patent Application No. 12150246.2.

European Search Report accompanied by Examiner's Preliminary Opinion, "Application No. EP 12150246", (Apr. 11, 2012), The Hague, total No. of pp. 12.

Response to Exam Report for European Application 12150246.2, dated Feb. 24, 2014.

* cited by examiner

# COOLING SYSTEM FOR AN OCCUPANT OF AN OCCUPANT SUPPORT AND A COOLING GARMENT

TECHNICAL FIELD

The subject matter described herein relates to occupant supports such as hospital beds and particularly to a cooling system associated with the occupant support for cooling the occupant and to a garment for cooling the occupant.

BACKGROUND

There are a number of common medical conditions that can cause a medical patient to perspire profusely. Such patients feel uncomfortably hot. Moreover, the presence of the perspiration weakens the patient's skin so that when the patient is resting on the mattress of a hospital bed he or she is at elevated risk of developing pressure ulcers at points where the skin contacts the mattress. The risk can be attenuated by employing a microclimate management (MCM) topper between the patient and the mattress. MCM toppers include an internal passageway which allows a stream of relatively cool air to flow beneath the patient and transport heat and perspiration to the environment. Such toppers also include an array of cooling holes which allow some of the air to escape from the passageway thereby cooling the patient directly and evaporating perspiration from his or her skin. However even high performing MCM toppers may not always provide sufficient relief. It is, therefore, desirable to devise other ways to cool the patient and evaporate perspiration, particularly if such ways are simple, inexpensive, reliable, convenient to use, and can take advantage of existing equipment and/or infrastructure likely to be present in a health care facility.

SUMMARY

Perspiration rate on a given "patch" of skin is thought to be a strong function of core body temperature, a less strong function of mean skin temperature and a relatively weak function of local skin temperature. Academic studies suggest that thermal stimuli applied to certain areas of the body, such as the palms and the areas served by the trigeminal nerves, have a disproportionately strong effect on core temperature and mean skin temperature. Therefore, it is possible to significantly reduce the level of perspiration released by the skin under the body (i.e. the skin in contact with the mattress) by cooling these thermally sensitive regions of the upper body. Accordingly, this application describes a cooling system for an occupant of an occupant support. The cooling system is a targeted cooling system comprising a coolant conduit having an inlet for receiving coolant from a source of coolant and an outlet for discharging the coolant to a destination. The conduit is nonpermanently and manually shape adjustable, shape stable subsequent to adjustment, and removably securable to one or both of the occupant support and the occupant. In one embodiment the destination is an ambient environment selected to achieve targeted coolant delivery to a localized region of the occupant's body. This application also discloses a glove to be worn by a user, e.g. a patient. The glove has at least one coolant intake and at least one of
a) a coolant passage extending from the coolant intake to an exhaust opening; and
b) a cooperative relationship with the user which defines a fluid pathway bounded in part by the glove and in part by the user.

The exhaust opening exhausts coolant from the passage to an ambient environment, to the fluid pathway, or to both. Coolant received by the fluid pathway discharges to an ambient environment.

BRIEF DESCRIPTION OF THE DRAWINGS

The foregoing and other features of the various embodiments of the cooling system described herein will become more apparent from the following detailed description and the accompanying drawings in which.

DETAILED DESCRIPTION

Figure 1:
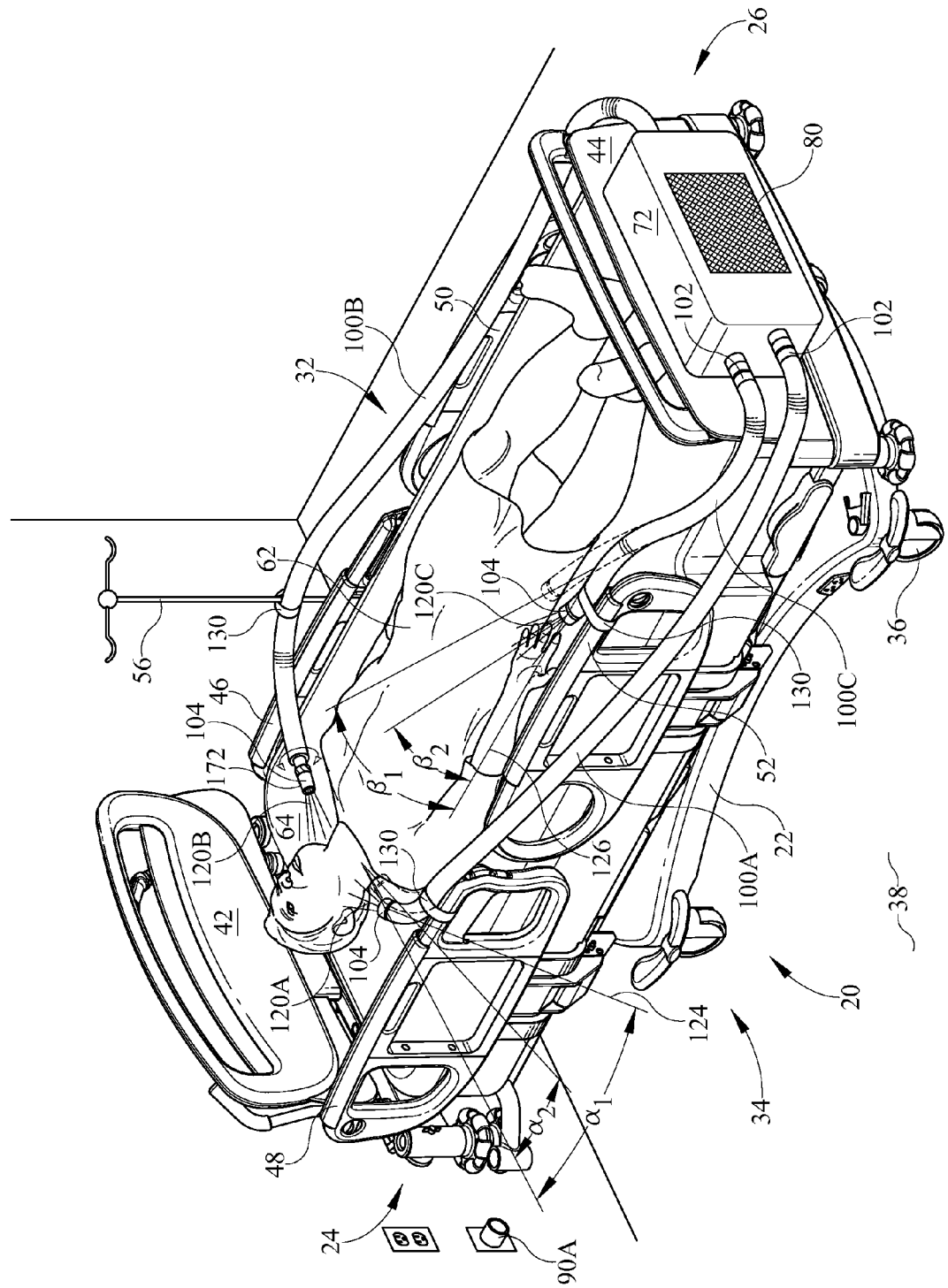
FIG. 1 is a perspective view of a hospital bed with three coolant conduits extending from a blower unit to individual destination locations, each in close proximity to areas of a patient's body where thermal stimuli are thought to have a disproportionate effect on core body temperature and/or mean skin temperature.
Figure 2:
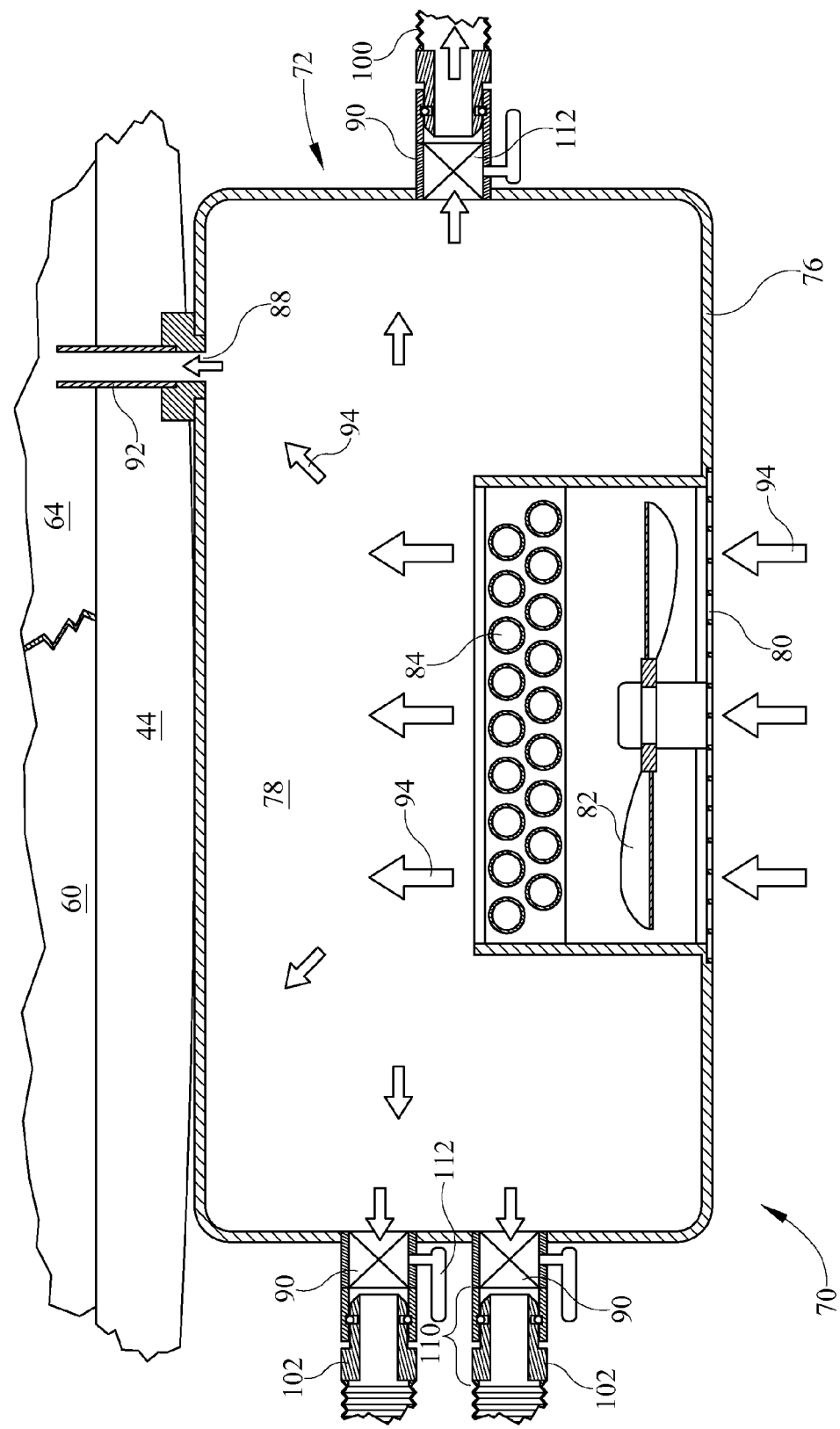
FIG. 2 is a plan view of the foot end of the bed and the blower unit showing additional detail and with the blower unit sectioned to expose components inside the blower housing.
Figure 3:
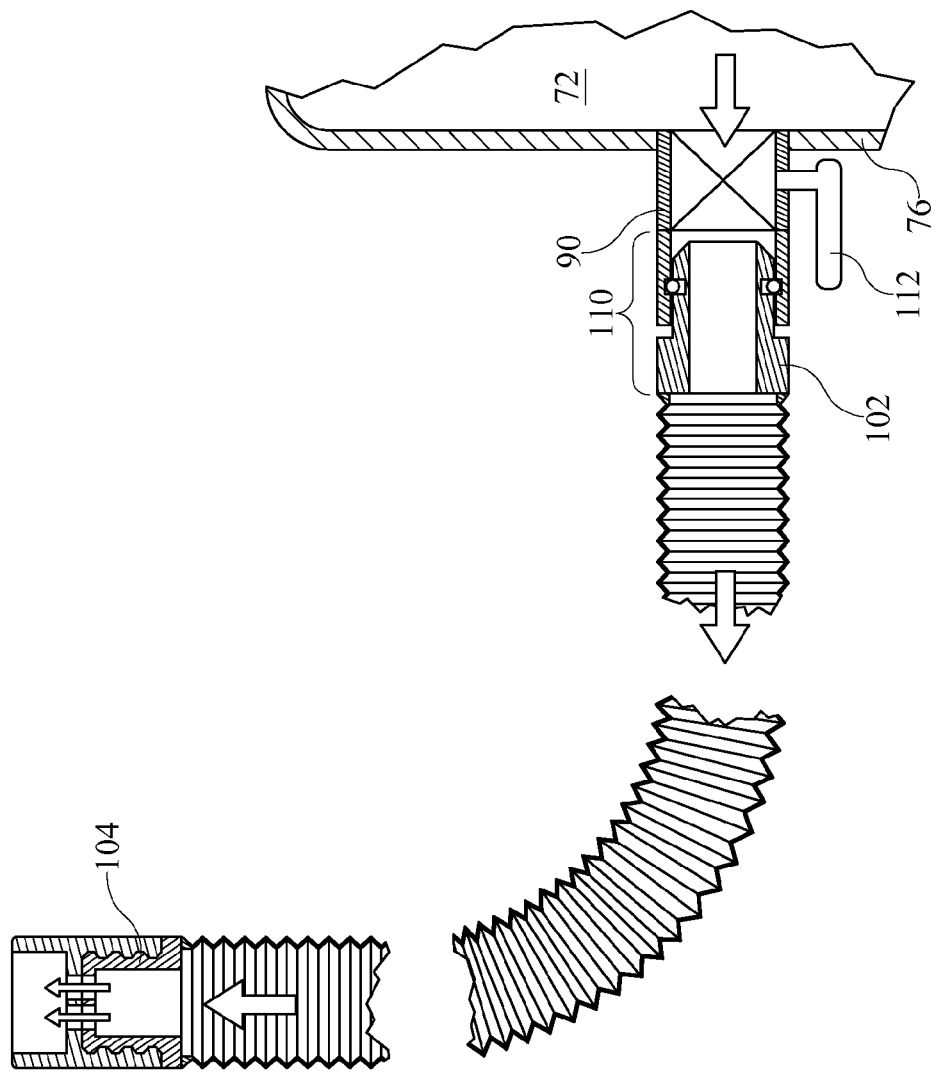
FIG. 3 is an enlarged view of a portion of FIG. 2.

Referring to FIGS. 1-3, an occupant support exemplified by a hospital bed 20 includes a frame 22 extending longitudinally from a head end 24 of the bed to a foot end 26 and laterally from a left side 32 to a right side 34. Casters 36 extend from the frame to floor 38. The frame also includes a headboard 42, a footboard 44, left and right head end siderails 46, 48, and left and right foot end siderails 50, 52. In the illustration the right siderails are in a raised or deployed position; the left siderails are in a lowered or stored position. An IV pole 56 extends vertically from the frame. The IV pole may be a permanent component of the frame or may be an auxiliary frame component that a caregiver attaches to the frame or detaches from the frame as needed. The means for attaching the IV pole to the frame may be a simple as a socket into which the caregiver places the bottom end of the pole. A mattress 60 for supporting an occupant 62 rests on the frame. An optional topper 64 rests on the mattress. One type of topper suitable for the illustrated bed is a powered topper. Powered toppers have an internal passageway. In operation, air flows through the passageway to help cool the occupant and evaporate perspiration.

A cooling system 70 includes a blower unit 72 mounted permanently or nonpermanently on the footboard or other part of the bed frame. The blower unit includes a housing 76 defining a plenum 78, an ambient air intake opening 80, a fan 82, an optional chiller 84 or other device for conditioning the ambient air, and one or more discharge ports 88, 90 downstream of the fan and chiller. Coolant 94 in the form of ambient air is drawn into the blower housing by fan 82, conditioned if the optional chiller 84 or other conditioning device is present and operating, and discharged through the discharge ports. The blower of FIGS. 1-3 has two types of discharge ports. Discharge port 88 supplies coolant to topper 64 by way of a topper supply hose 92. Discharge ports 90 supply coolant to respective coolant conduits 100 (with letters such as A, B, C appended to the reference numeral to designate specific conduits). Each conduit 100 has an inlet 102 for receiving coolant from a source thereof, such as blower 72. Inlet 102 of each conduit 100 is connected to a blower discharge port 90 by a suitable connector such as the quick connect fittings 110 seen in FIGS. 2-3. A valve 112 regulates fluid flow through each port 90 and, in the event a conduit is connected to the port, into the conduit intake 102. Each conduit also has an outlet 104 for discharging the coolant to a destination. In FIG. 1 the destination is the ambient environment in the vicinity of the occupant and sufficiently close to the occupant to provide effective cooling to selected locations on the occupant's body.

Blower 72 is illustrated as a local blower mounted on the footboard. However the blower could also be a unit not mounted on the bed. One example is a blower located in a utility room with ductwork extending from the blower unit to a discharge port 90A (FIG. 1) on a hospital room wall or headwall.

The blower of FIGS. 1-3 is shared by the cooling conduits 100 and by at least one other component of the occupant support, namely topper 64. Alternatively, the blower could be dedicated to serving only the cooling conduits of the cooling system.

Each conduit 100 is nonpermanently and manually shape adjustable and is shape stable subsequent to adjustment. In other words a human user can bend the conduit to a desired shape (manually shape adjustable), after which the conduit holds that shape (shape stable subsequent to adjustment) until a user bends it into another stable shape (nonpermanently shape adjustable) The illustrated conduits achieve these characteristics as a result of a ribbed construction seen, for example, in FIG. 3. Because of the shape adjustability the caregiver can route conduit along a convenient selected path from the blower discharge port 90 to any destination location at which the caregiver desires to place the outlet 104. The destination location is one that is close enough to a targeted location on the occupant's body that coolant issuing from the conduit outlet can provide effective cooling at the targeted location. Two locations thought to be satisfactory targets are the palms of the occupant's hands and the regions served by the trigeminal nerve, e.g. the neck, jaw and cheek. For example, conduit 100A extends along the right side of the bed outboard of the right foot end siderail, over the top of the right head end siderail and terminates with its outlet 104 at a destination 120A proximate the occupant's right jaw. Conduit 100B extends along the left side of the bed inboard of the left foot end siderail, makes a sharp inward turn at IV pole 56 and terminates with its outlet at a destination 120B near the occupant's left jaw. Conduit 100C extends longitudinally and vertically along the foot end of the right side of the mattress, then a short distance along the top of the mattress, and terminates with its outlet 104 at a destination 120C near the palm of the occupant's right hand. The shape adjustability of the conduit permits a user to orient the outlet end 104 of the conduit at a desired orientation. For example, FIG. 1 shows the outlet end of conduit 100A oriented at different angles $\alpha_1$ (solid lines) and $\alpha_2$ (phantom lines) in the same horizontal plane relative to an arbitrary, coplanar reference line 124. FIG. 1 also shows the outlet end of conduit 100B oriented at different angles $\beta_1$ (solid lines) and $\beta_2$ (phantom lines) in the same vertical plane relative to an arbitrary, coplanar reference line 126. FIG. 1 shows the differences in orientation angles $\alpha$ and $\beta$ restricted to a single plane merely for illustrative convenience. In practice, no such restriction need be observed.

Referring to FIGS. 1 and 4-7, a securement feature 130 renders each cooling system conduit 100 removably securable to the occupant support, to the occupant, or to both. In FIGS. 4A and 4B the securement feature is a clamp 132 having a band 134 circumscribing the conduit 100 and a pair of deflectable arms 136 extending from the band. In use, the arms deflect so that a user can snap the clamp onto a siderail, as shown in the illustrations, or onto some other frame component. The deflectable arms then grip the siderail until the user disengages the clamp by pulling it away, causing the arms to deflect and release their grip.

Figure 4C:
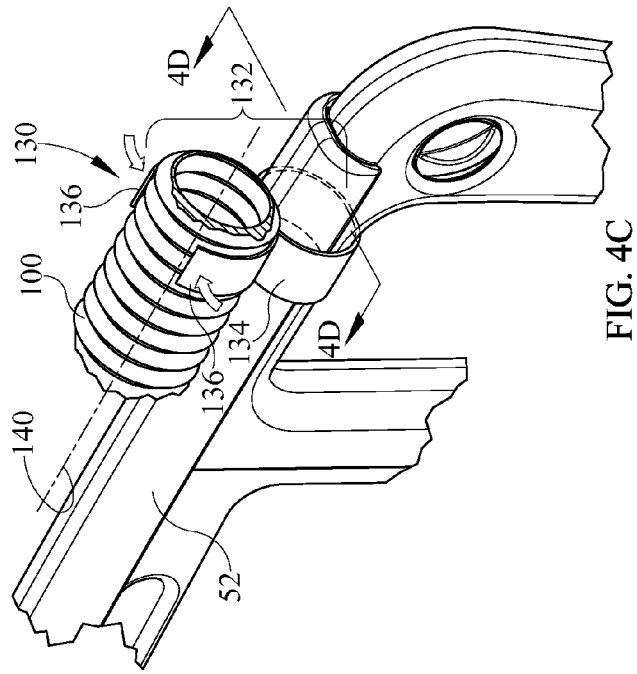
FIGS. 4A-4E are views showing a securement feature in the form of clamps of different styles for securing coolant conduits to a bed frame component.
Figure 4A:
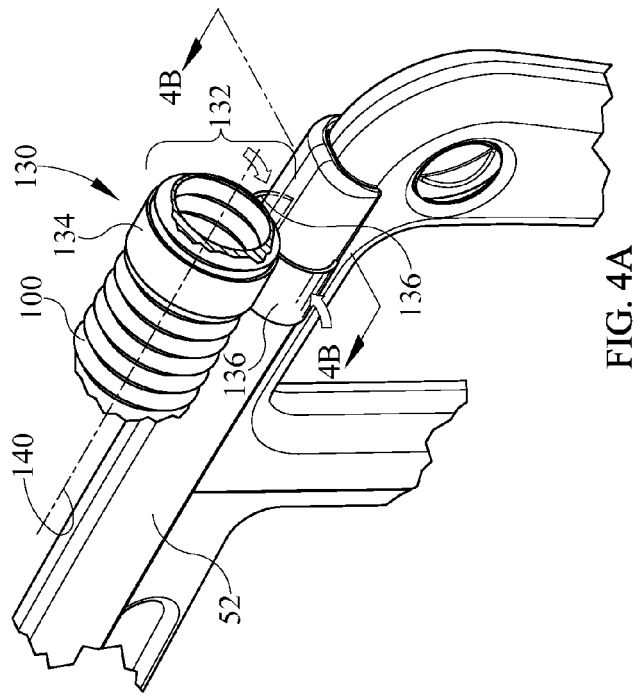
Figure 4D:
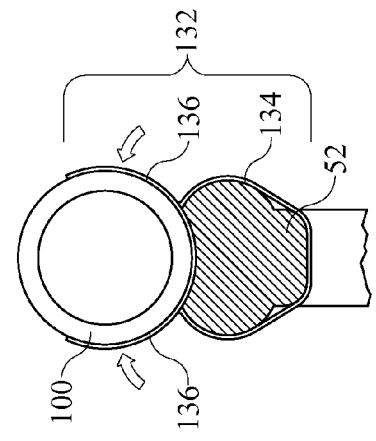
Figure 4E:
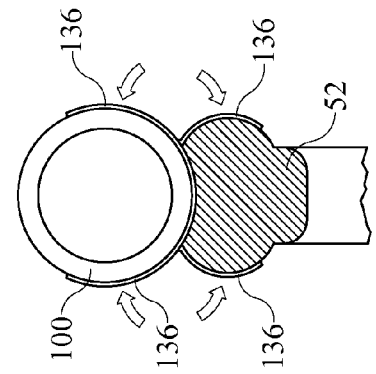
Figure 4B:
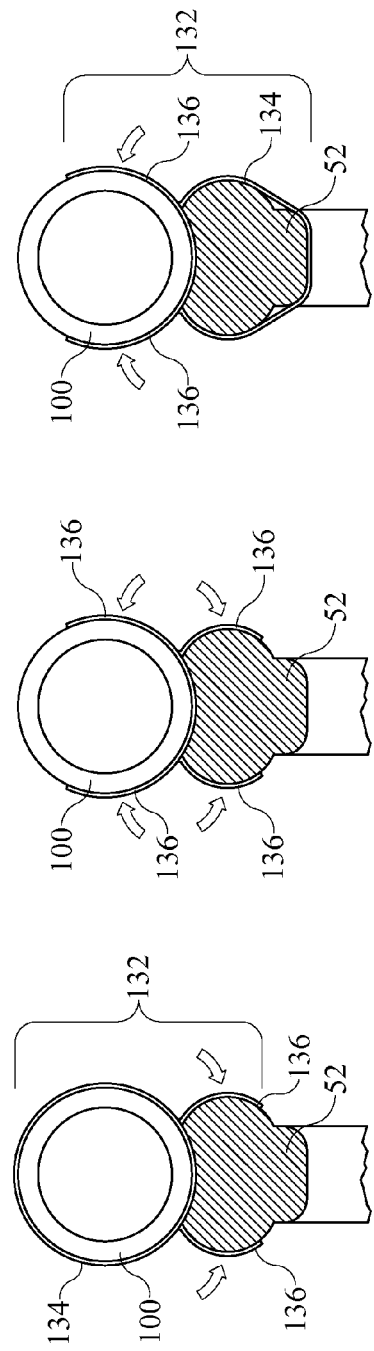

In one embodiment of clamp 132, band 134 fits tightly around the conduit to prevent slippage of the conduit relative to the band in the local direction of the conduit axis 140. As a result, the position of the clamp relative to the conduit is fixed. In an alternative embodiment the band fits less tightly around the conduit so that a user can slide the conduit through the clamp band or slide the clamp band along the conduit to position the clamp at a desired location along the conduit. The latter embodiment is nevertheless designed to exhibit some amount of slip resistance so that the clamp, once positioned at a desired position along the conduit, tends to remain at that position unless intentionally moved by a user. In a third embodiment the clamp may include a lock or latch that can be released to allow relative movement of the conduit and clamp or engaged to prevent or resist such movement. Irrespective of whether the clamp is fixed or moveable, the clamp of FIGS. 4A and 4B is associated principally with the conduit 100 given that the clamp is not as conveniently removable from the conduit as it is from the siderail. Alternatively, as seen in FIG. 4C-4D, the roles of the band and arms could be reversed so that the band 134 circumscribes the siderail (or other frame component) and the arms 136 grip the conduit. In such an arrangement the clamp is associated principally with the occupant support given that the clamp is not as conveniently removable from the siderail or other frame component to which it is attached as it is from the conduit. Yet another option, seen in FIG. 4E, is a clamp comprising two sets of arms 136 so that the clamp can be readily snapped onto or removed from both the conduit and the frame component.

Figure 5:
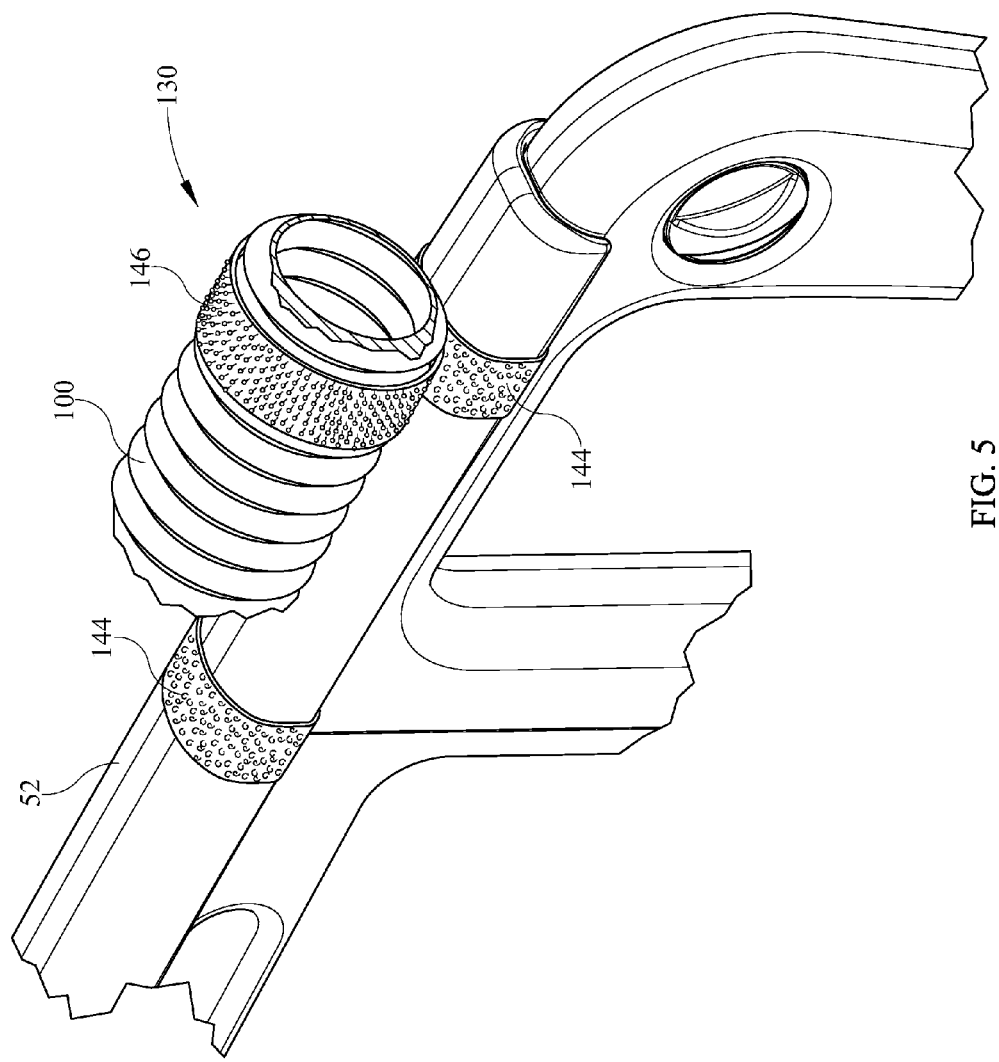
FIG. 5 is a perspective view similar to that of FIG. 4A showing a hook and loop securement feature.

FIG. 5 shows an example of a VELCRO® hook and loop securement feature 130. The securement feature comprises a patch 144 of hooks at one or more locations on the siderail or other frame component and a patch 146 of loops at one or more locations on the conduit. As with the clamp securement feature the hook and loop patches can reside at a fixed location along the siderail and/or conduit, can be slideable along the siderail and/or conduit, or can be designed to be removed from and installed on the siderail and/or conduit at the discretion of a user.

Figure 6:
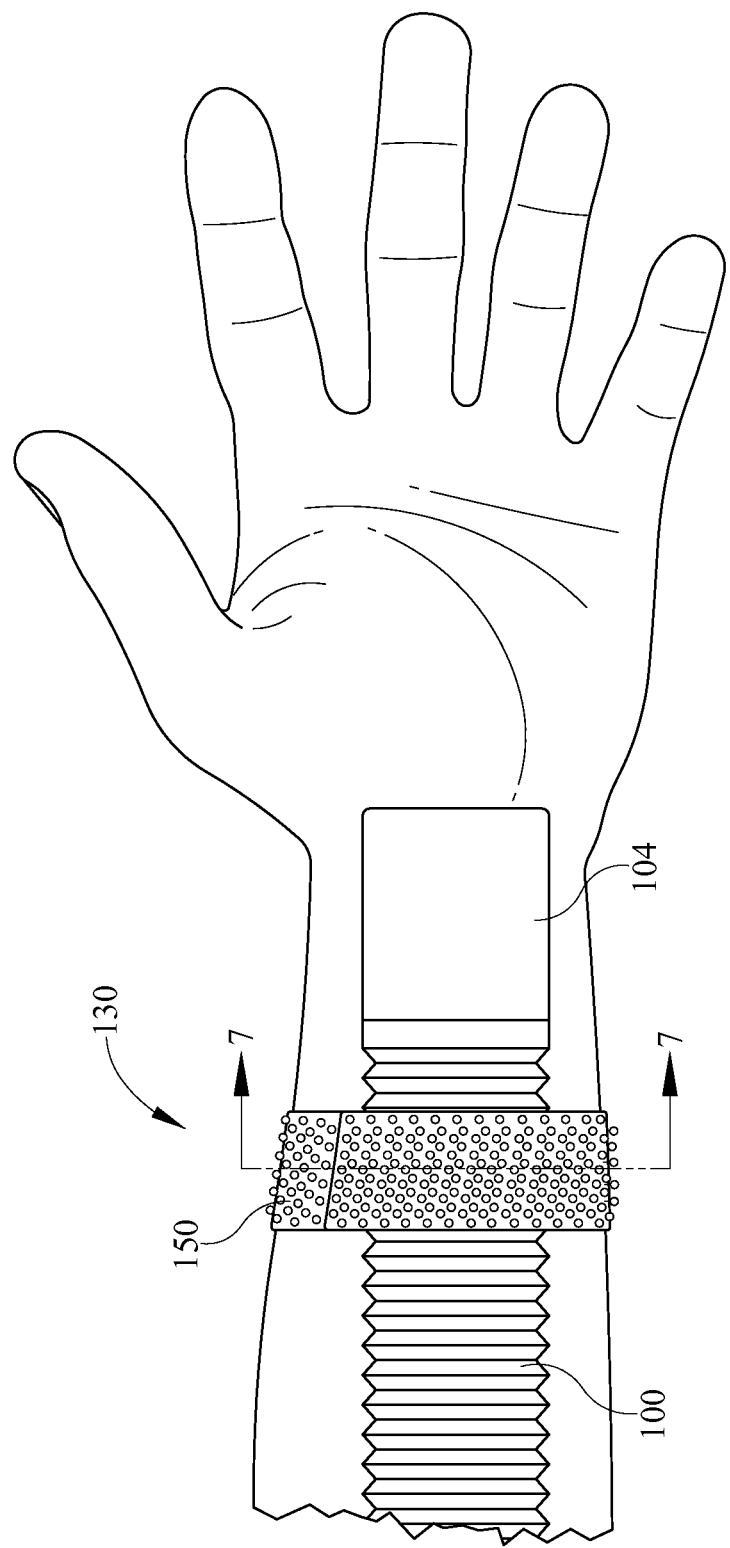
FIG. 6 is a plan view of the palm and lower arm of a bed occupant showing a hook and loop securement feature used to secure a coolant conduit to the patient's arm.
Figure 7:
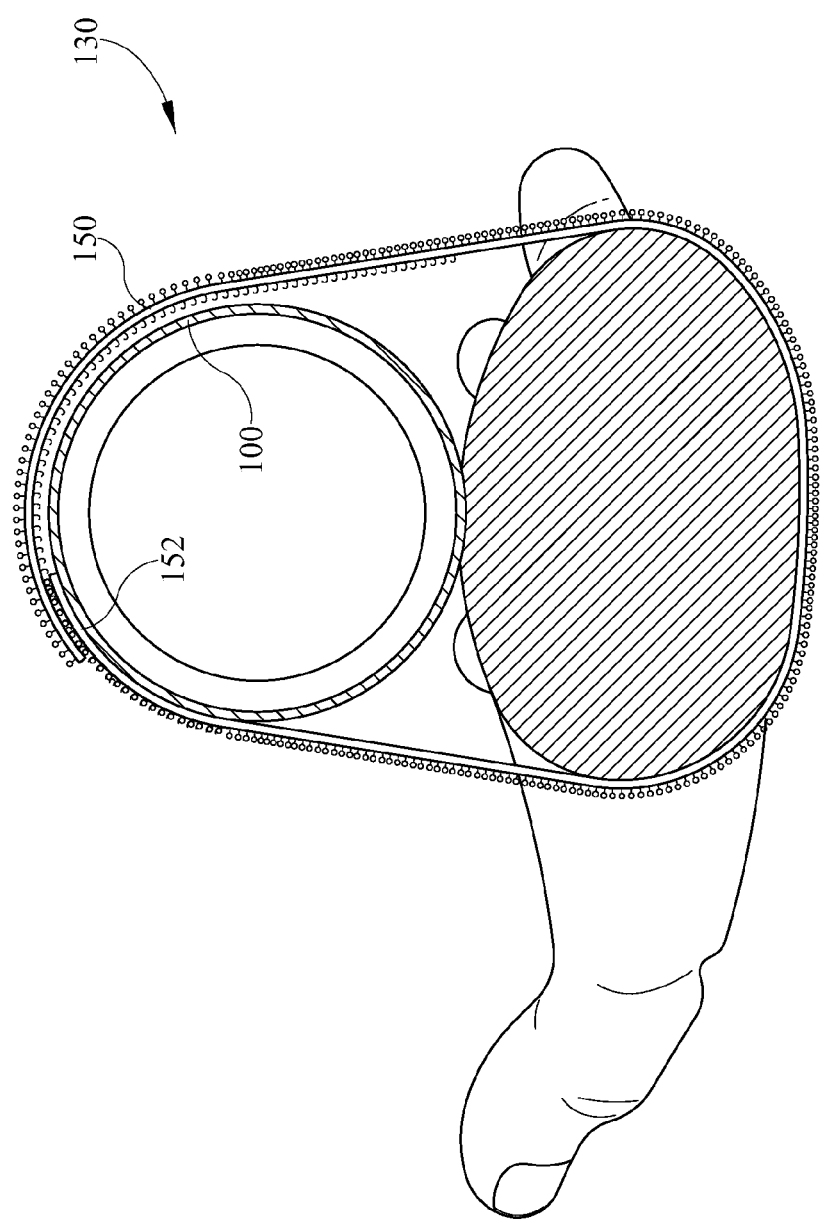
FIG. 7 is a view in the direction 7-7 of FIG. 6.

FIGS. 6-7 show the outlet end of a conduit 100 secured to an occupant's wrist by another type of hook and loop securement feature 130 so that even if the occupant changes position outlet 104 remains in a fixed position relative to the palm of the occupant's hand and coolant issuing from conduit outlet 104 flows reliably across the occupant's palm. The illustrated securement is a VELCRO® strap 150 attached to conduit 100 at an attached end 152 and sufficiently long that it can wrap around the occupant's wrist and be secured to itself to hold the conduit in place.

Securement features other than clamps or hook and loop fasteners may also be used.

Figure 8:
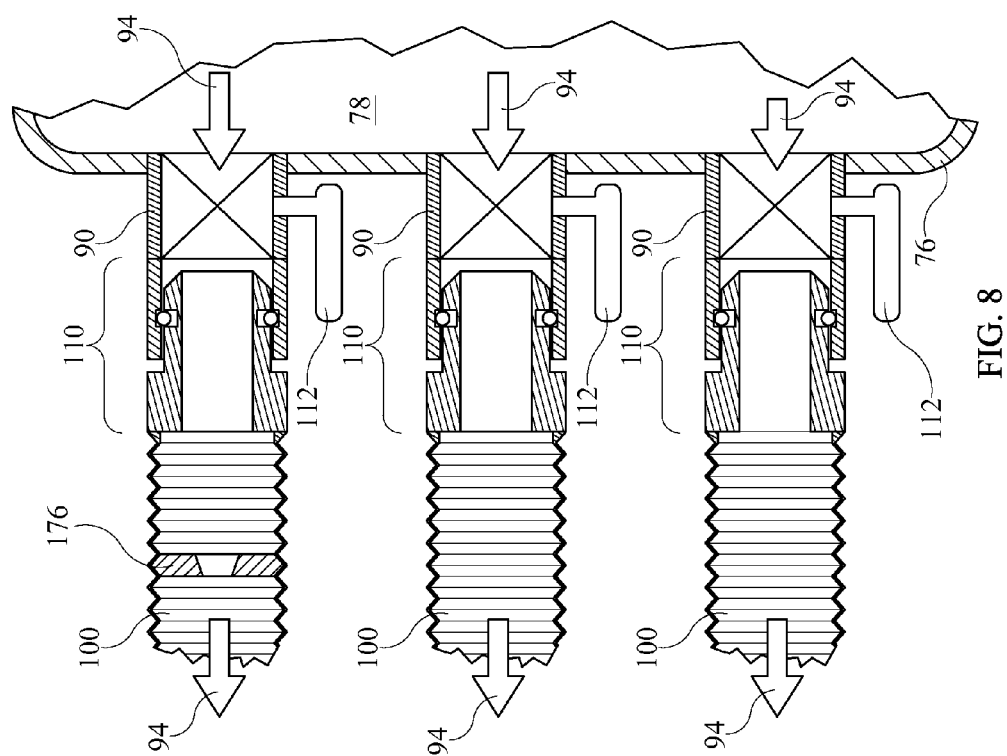
FIG. 8 is a plan view showing a one to one correspondence between multiple blower discharge ports and multiple cooling system conduits.
Figure 9:
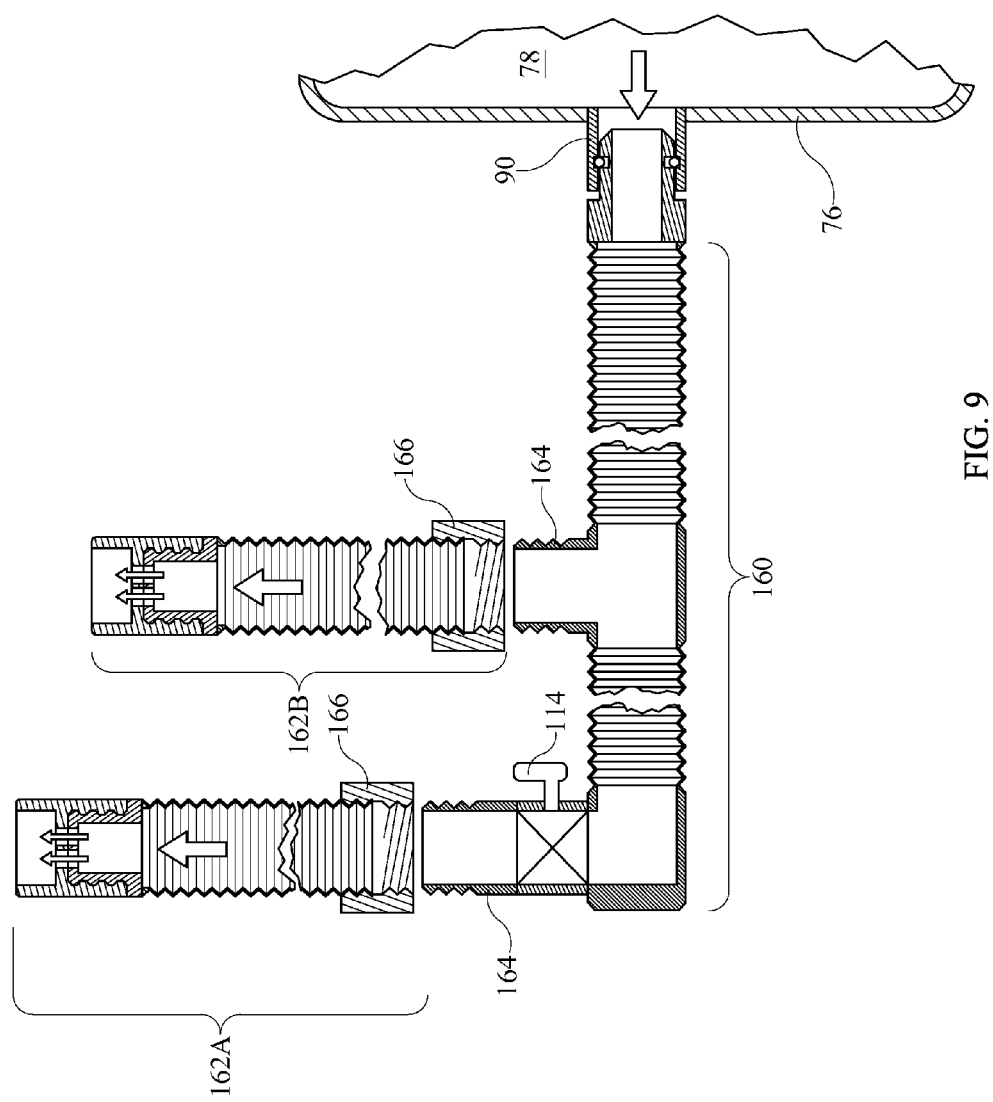
FIG. 9 is a plan view similar to that of FIG. 8 showing an arrangement in which a single blower discharge port supplies coolant to a conduit comprising a trunk and multiple branches.
Figure 10:
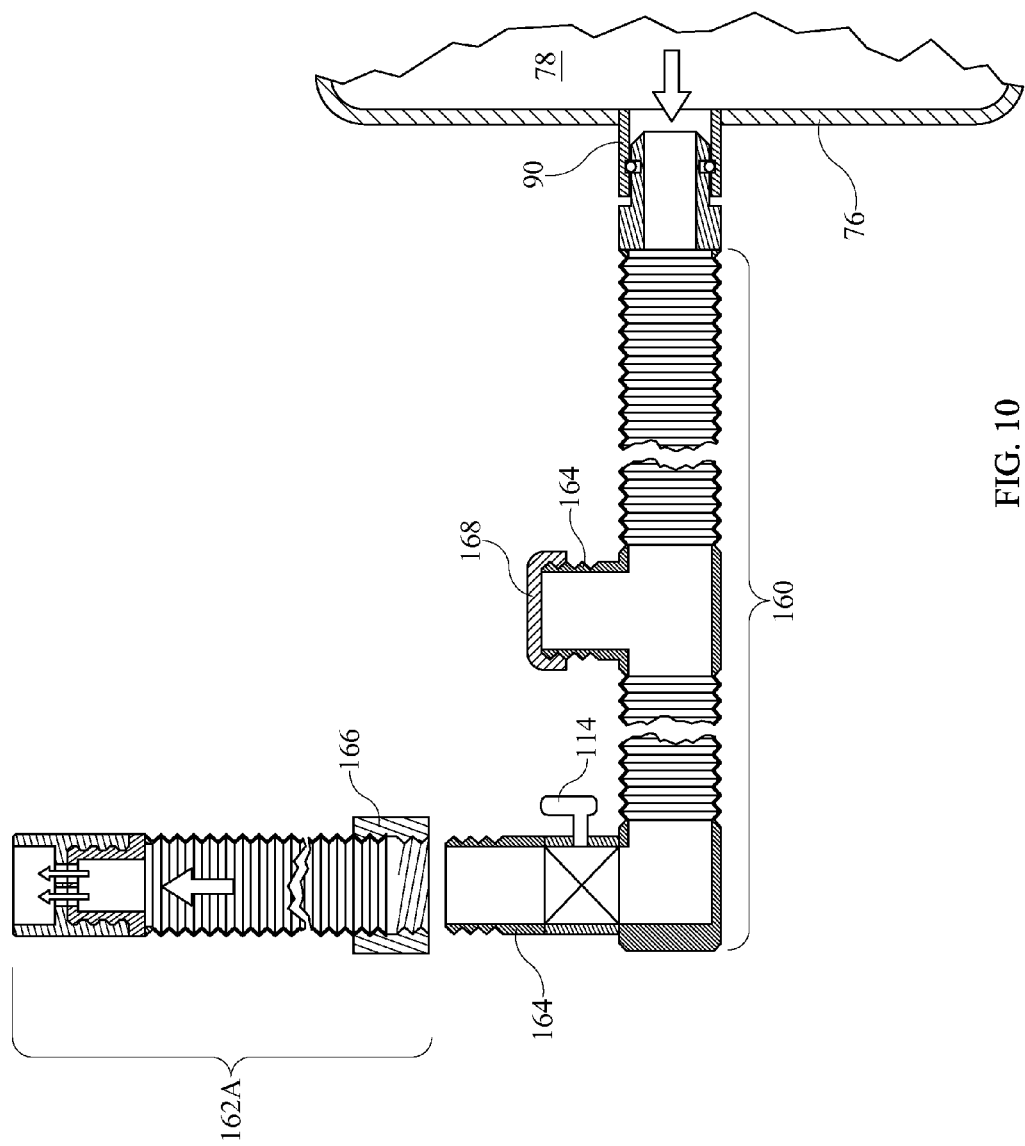
FIG. 10 is a view similar to that of FIG. 9 with one of the branch conduits having been disconnected and replaced by a cap.

FIGS. 8-10 show a nonexhaustive set of blower and conduit options. FIG. 8, like FIG. 1, shows a one to one correspondence between multiple blower discharge ports 90 and multiple cooling system conduits 100. Each conduit extends to a distinct destination, such as destinations 120A, 120B, 120C seen in FIG. 1. A valve 112, illustrated as a simple manual valve, regulates fluid flow out of blower plenum 78. Quick connect couplings 110 effect attachment of each conduit to the blower discharge parts. FIG. 9 shows an arrangement in which a single blower discharge port 90 supplies coolant to a conduit 100 which comprises a trunk 160 and multiple branches 162A, 162B. A valve 114 regulates flow through branch 162A. Flow through branch 162B is unregulated. Trunk 160 carries coolant for multiple destinations, each of which is served by a dedicated branch. Threaded male and female fittings 164, 166 effect attachment of each branch to the trunk, although some or all of the branches could be permanently attached to the trunk. FIG. 10 shows the arrangement of FIG. 9 with branch conduit 162B having been disconnected and replaced by a cap 168.

The flow regulating valves 112, 114 may be simple on/off valves, such as a solenoid controlled valve or could be a modulating valve depending on the requirements for regulating coolant flow parameters, such as mass flow rate and/or distribution. The valve may be positioned at the blower discharge port as seen in FIGS. 2, 3 and 8 (valve 112), at a juncture near a conduit trunk and a conduit branch as in FIGS. 9-10 (valve 114), or at any other convenient locations. One location that may be especially satisfactory is at the conduit outlet where, as seen in FIG. 1, conduit 100B includes a rotary valve or nozzle 172 that allows a user to adjust coolant mass flow rate at the point of use while he or she is standing near that point of use. A valve or nozzle at the conduit outlet could also be of the type that allows adjustment of the spray pattern of the coolant issuing from the outlet.

In at least some applications it may be desirable to include a nonadjustable flow restrictor instead of or in addition to any adjustable flow regulating valves. Such a flow restrictor, in the form of a simple orifice plate 176, is shown in the uppermost conduit of FIG. 8. Use of such a flow restrictor may be especially desirable if the blower supplies air to not only the coolant conduits 100, but also to another component of the occupant support, such as low air loss topper 64. The flow restrictor chokes coolant flow to the cooling system conduit in order to preferentially feed the topper and prevent the topper from being starved for coolant.

Figure 11:
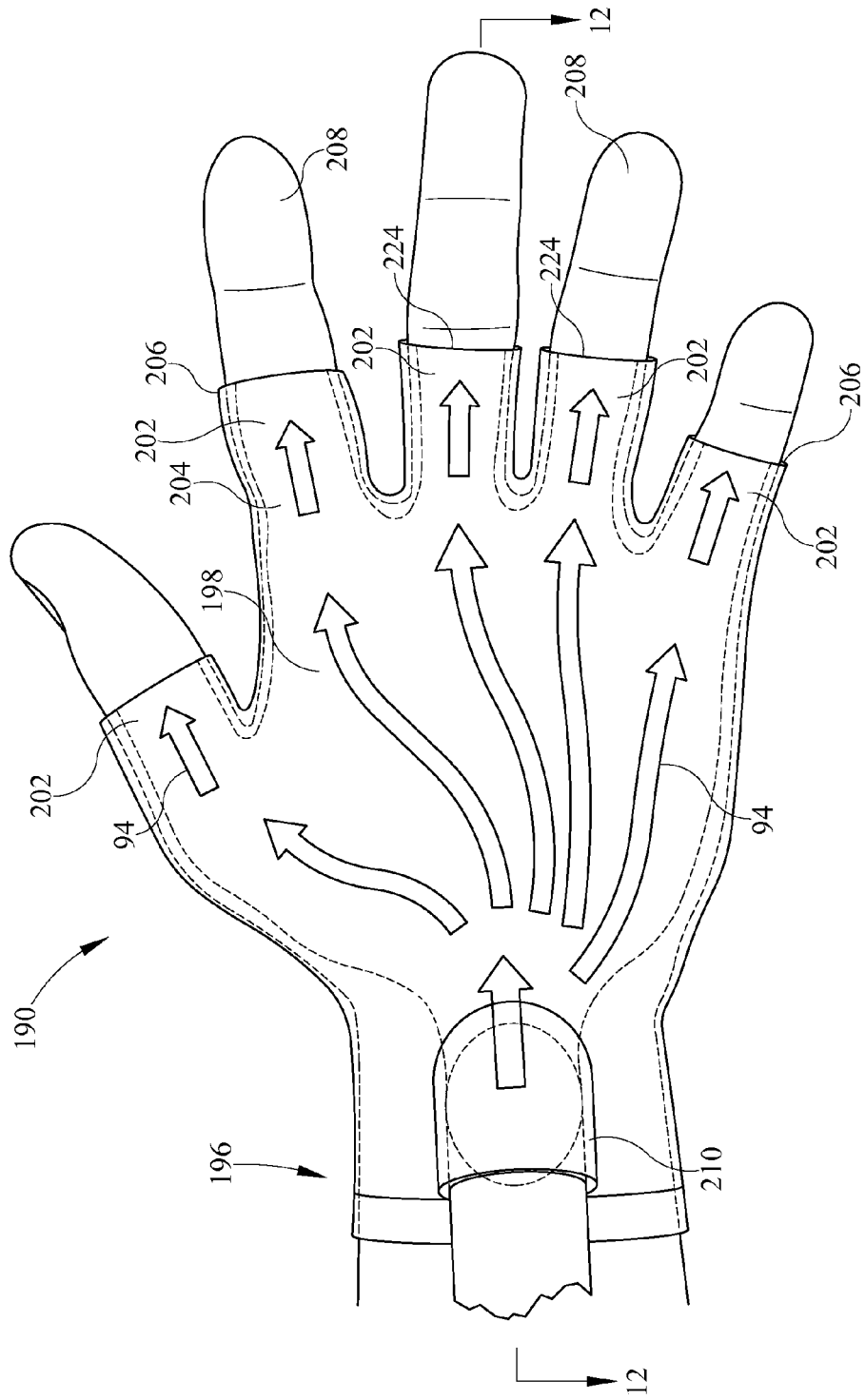
FIGS. 11 and 12 are a plan view and a cross sectional side elevation view respectively of a glove to be worn by a user wherein the glove cooperates with the wearer's hand to define a fluid pathway bounded in part by the glove and in part by the wearer, the pathway extending from an intake to a vent for exhausting coolant to the ambient environment and wherein the vent is defined by annuli formed by the wearer's fingers and the distal ends of the glove fingers.
Figure 12:
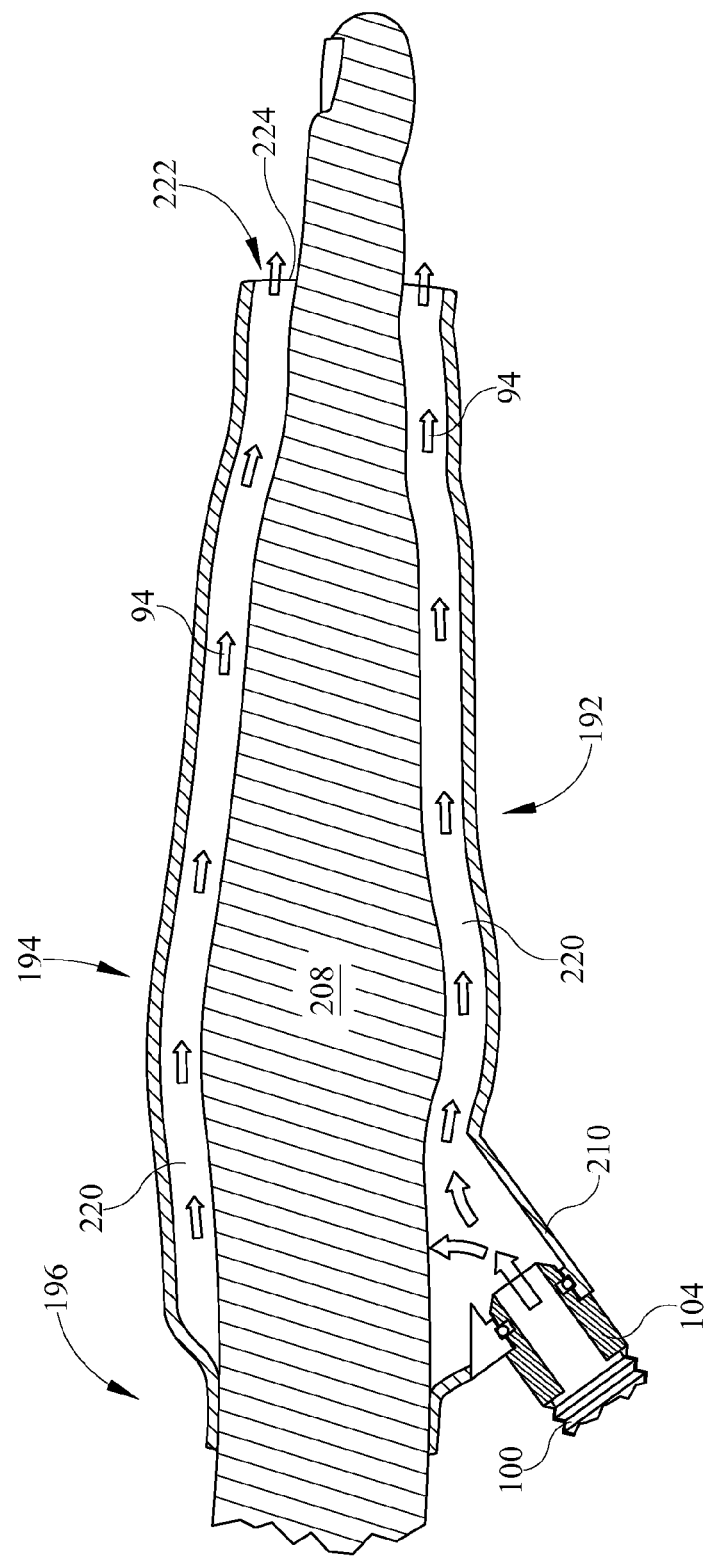

Referring to FIGS. 11-12 the cooling system can also include a garment, such as glove 190, wearable by the user. The glove includes a palm side 192, a back side 194, a wrist end 196, a metacarpal region 198, and fingers 202 each having a metacarpal end 204 and a distal end 206. The fingers have a slightly oversized diameter relative to an occupant's finger diameter so that the glove fingers fit loosely around the wearer's fingers 208 when the glove is being worn. The glove fingers are also foreshortened and open at the distal end so that the wearer's fingers extend beyond the distal ends of the glove fingers. The glove also includes a coolant intake fitting 210 attached to the glove on the palm side thereof near wrist end 196. Outlet end 104 of a coolant conduit is permanently or removably attached to the intake 210 so that the intake is the destination of the coolant discharged from the blower outlet.

The glove provides a coolant flowpath for coolant discharged by the coolant conduit. As will be appreciated in view of the discussion below, the flowpath may comprise a fluid pathway, a fluid passage, or a combination of a fluid pathway and a fluid passage.

When worn by a bed occupant, the glove cooperates with the wearer's hand to define a fluid pathway 220 bounded exclusively in part by the glove and in part by the wearer. The pathway extends from intake 210 to a flowpath vent, specifically a pathway vent 222 defined by the annuli 224 formed by the wearer's fingers and the distal ends of the glove fingers. In operation, the fluid pathway receives coolant from intake 210, conducts the coolant along the wearer's hand, and discharges the coolant to the ambient environment by way of vent 222. The pathway could extend along both the palm and the back side of the occupant's hand as depicted in FIG. 12, however available research suggests that targeted cooling is more effective along the palm than along the back side of the hand. Accordingly, it is believed that a glove that cooperates with an occupant's hand to define a fluid pathway only along the palm side of the wearer's hand would be satisfactory.

Figure 13:
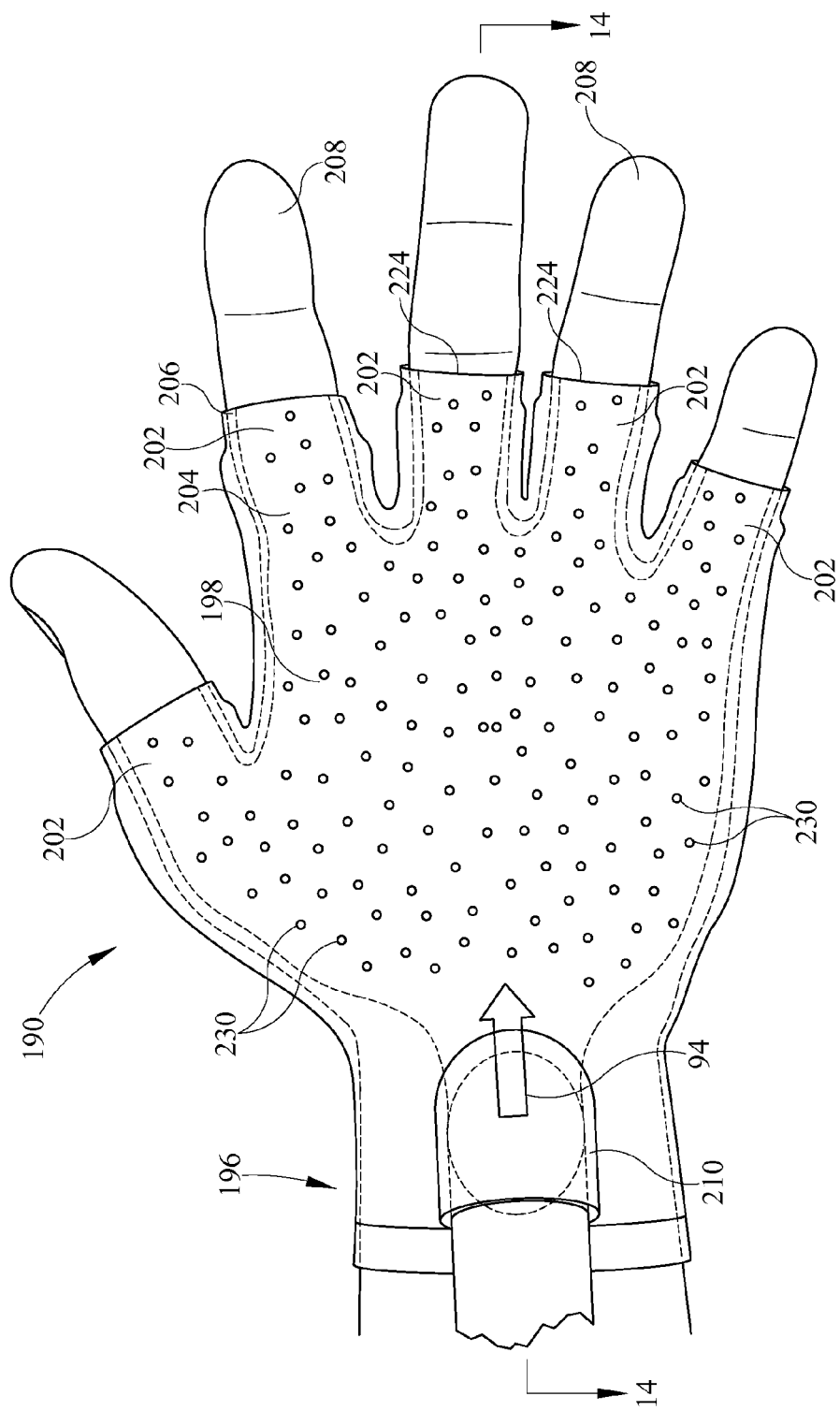
FIGS. 13-14 are a plan view and a cross sectional side elevation view respectively of a glove similar to the glove of FIGS. 11-12 wherein the vent for exhausting coolant to the ambient environment is defined by an array of vent holes.
Figure 14:
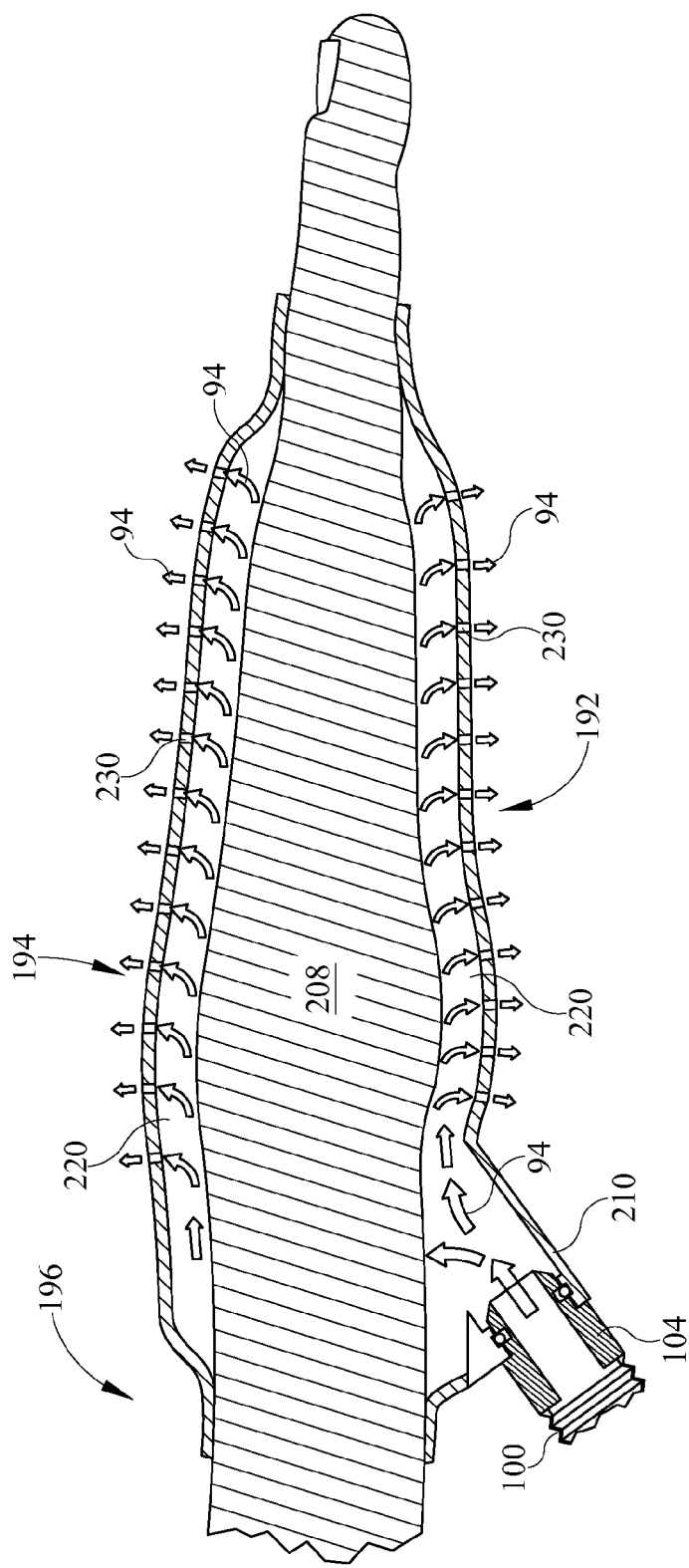

Referring to FIGS. 13-14, in another variant of glove 190 the distal ends 206 of glove fingers 202 fit snugly around the wearer's fingers. In addition, a series of vent holes 230 penetrates the glove and collectively define the pathway vent 222 so that the fluid pathway 220 extends from the intake 210 to a vent 222 defined collectively by the vent holes 230. As with the variant of FIGS. 11-12, the fluid pathway receives coolant from intake 210, conducts the coolant along the wearer's hand, and discharges the coolant to the ambient environment by way of vent 222 represented by the vent holes 230. Because the targeted cooling is thought to be more effective along the wearer's palm than along the back side of the wearer's hand, it may be sufficient to provide the vent holes only on the palm side of the glove.

Figure 15:
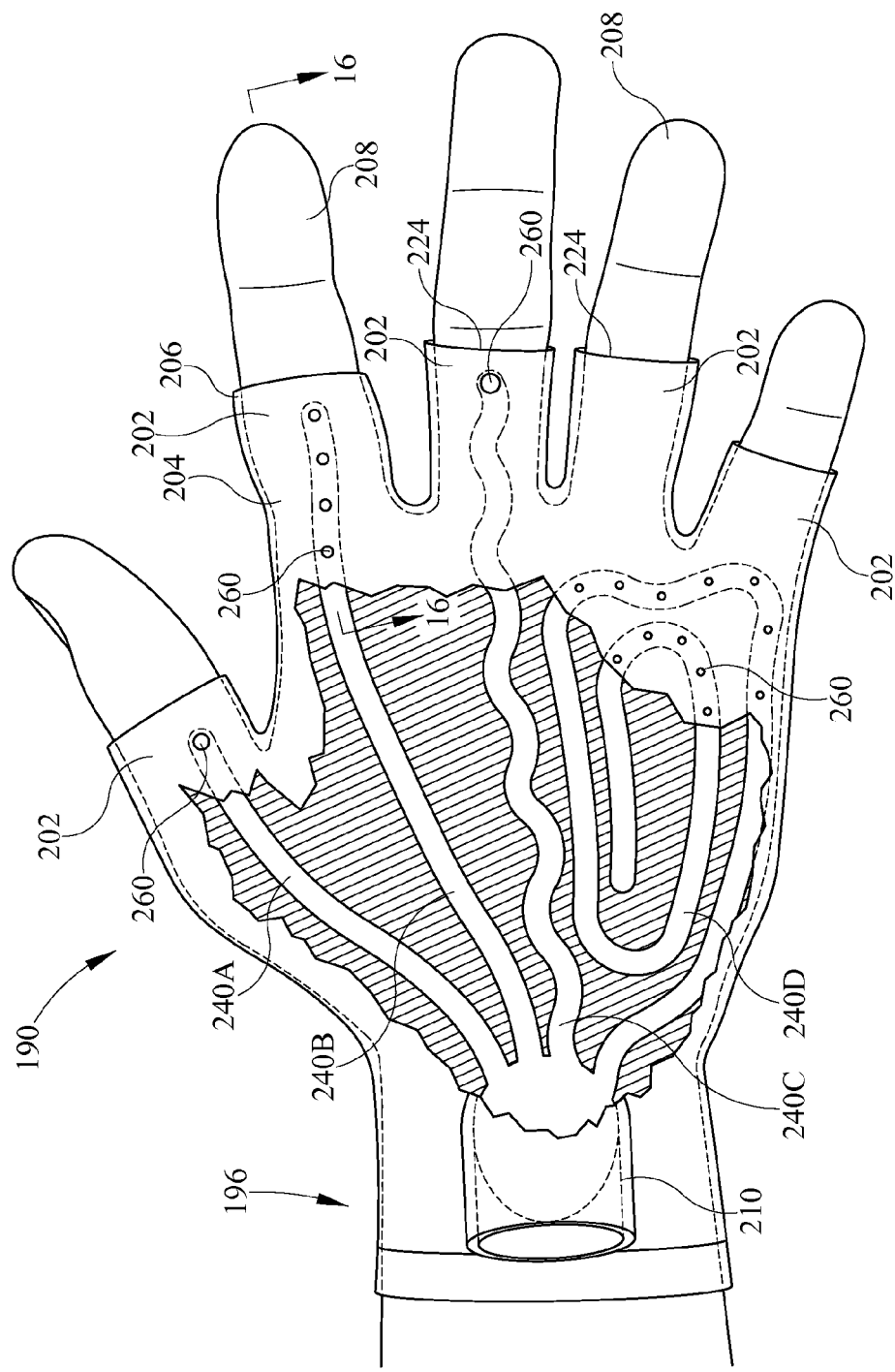
FIGS. 15-16 are a partially sectioned plan view and a cross sectional side elevation view respectively of a glove to be worn by a user and having fluid passages extending through the interior of the glove between inner and outer layers of glove material, each passage including one or more exhaust openings for exhausting coolant from the passage to the ambient environment.
Figure 16:
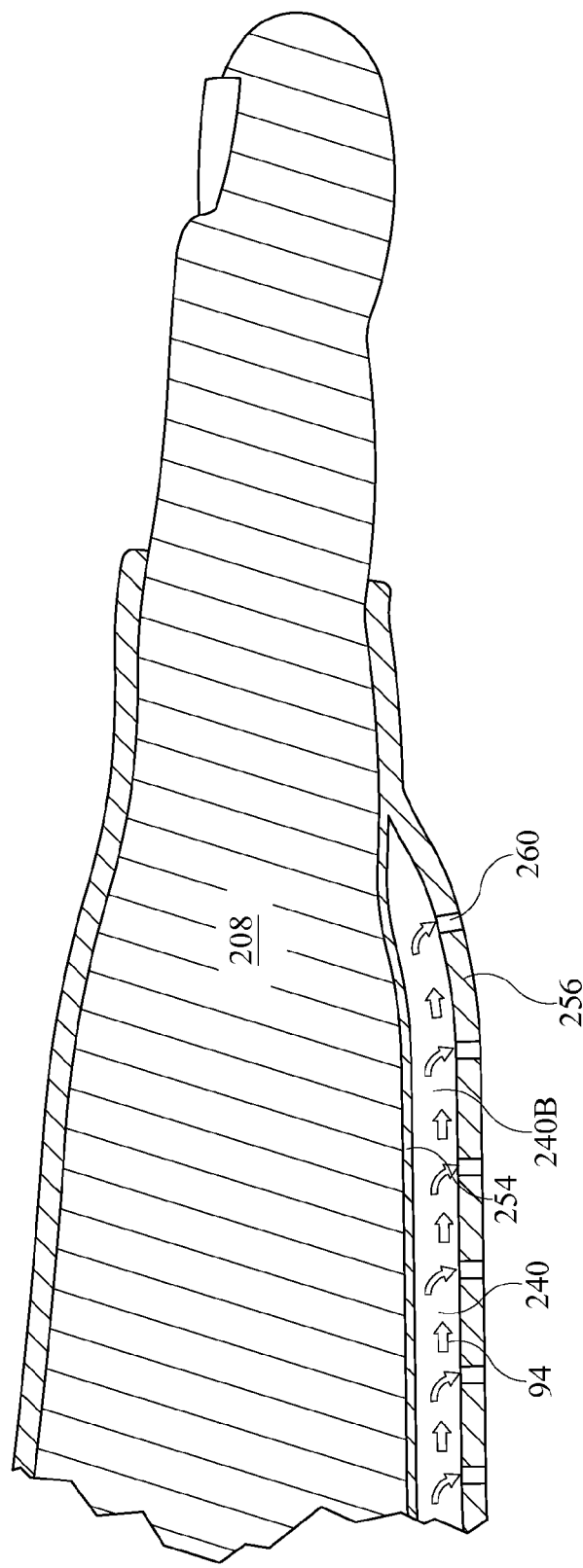

Referring to FIGS. 15-16, another variant of glove 190 features fluid passages 240A, 240B, 240C, 240D, extending through the interior of the glove between inner and outer layers 254, 256 of glove material. Each passage has one or more exhaust openings 260 for exhausting coolant from the passage to the ambient environment. Passage 240A is a linear or quasi-linear passage having a single exhaust opening 260 at its distal end. Passage 240B is a similar passage having exhaust openings 260 distributed along its length from the wrist end of the passage to the distal end of the passage. Passage 240C is a serpentine passage with a single exhaust opening 260 at its distal end. Passage 240D is a spiral passage with exhaust openings 260 distributed along its length. The various passage geometries are shown in a single glove for economy of illustration. In practice, a glove would likely employ only one type of passage geometry.

The illustrated passage geometries are not an exhaustive collection of possible geometries. The quantity of passages may be more or fewer than shown. In operation, coolant flows from the glove intake 110, through the passages 240, and out the exhaust openings 260 without directly contacting the wearer's skin. As a result, heat flows through the inner material layer and into the coolant stream which transports the heat to the environment. The glove designer can select a material for inner layer 254 having a thermal conductivity compatible with the desired rate of heat transfer from the occupant's hand. To the extent that it is also desired to remove perspiration from the wearer's skin, the inner layer is also vapor permeable. Once again, available research suggests that it is probably satisfactory to provide coolant passages only along the palm side of the glove.

Figure 17:
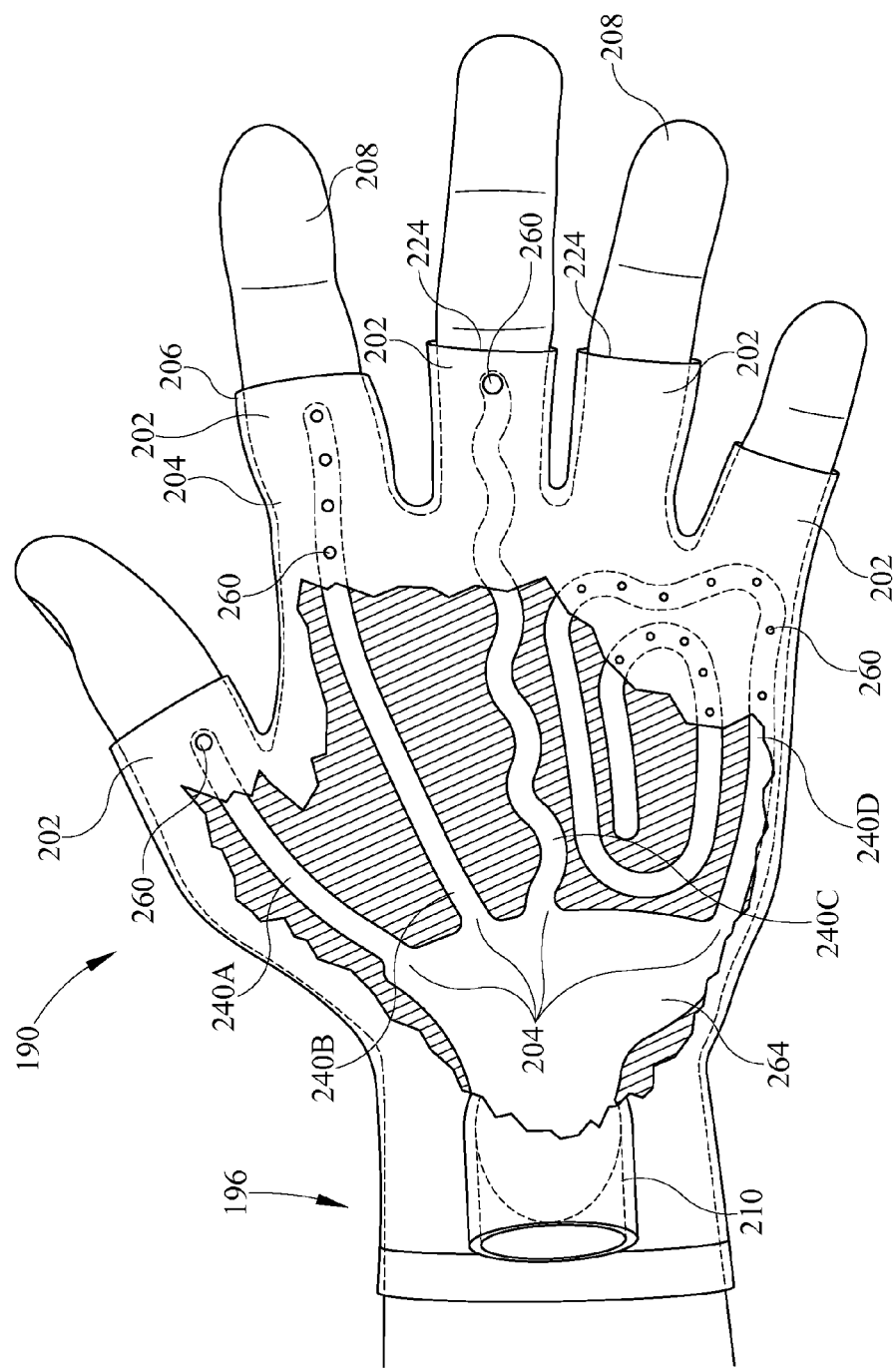
FIG. 17 is a view similar to that of FIG. 15 including a glove plenum serving as a fluid distributor to help distribute coolant laterally to the individual passages.

FIG. 17 show a glove similar to that of FIGS. 15-16 including a glove plenum 264 streamwisely between glove coolant intake 210 and the metacarpal ends 204 of the individual passages. The plenum serves as a fluid distributor to help distribute coolant laterally to the individual passages.

Figure 18:
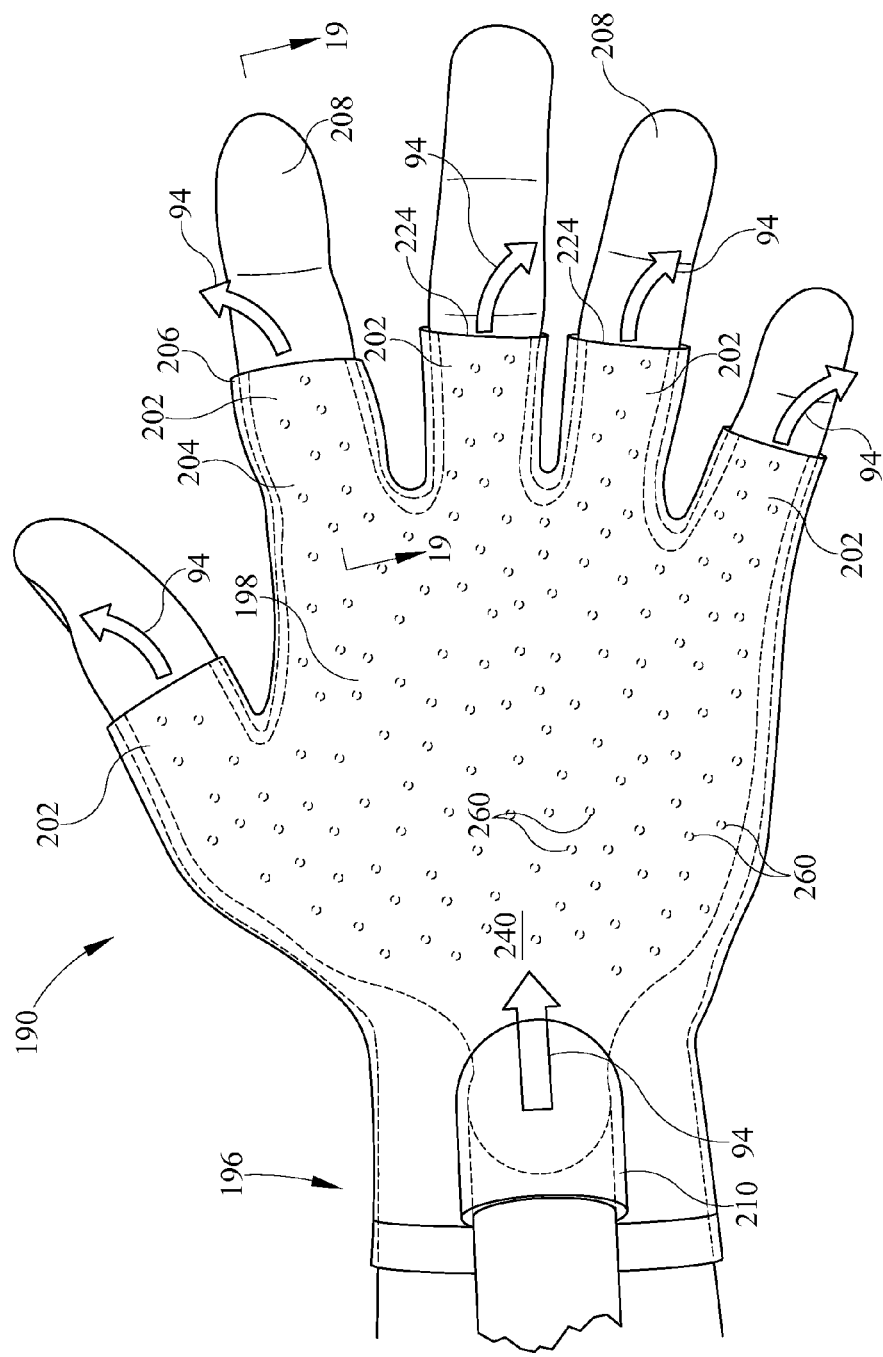
FIGS. 18-19 are a plan view and a cross sectional side elevation view respectively of a glove including a passage extending through the interior of the glove between inner and outer layers of glove material and a coolant pathway bounded in part by the glove and in part by the wearer's hand, the passage including an array of exhaust openings for exhausting coolant from the passage to the pathway, the pathway extending to a vent for exhausting the coolant to the ambient environment and wherein the vent is defined by annuli formed by the wearer's fingers and the distal ends of the glove fingers.
Figure 19:
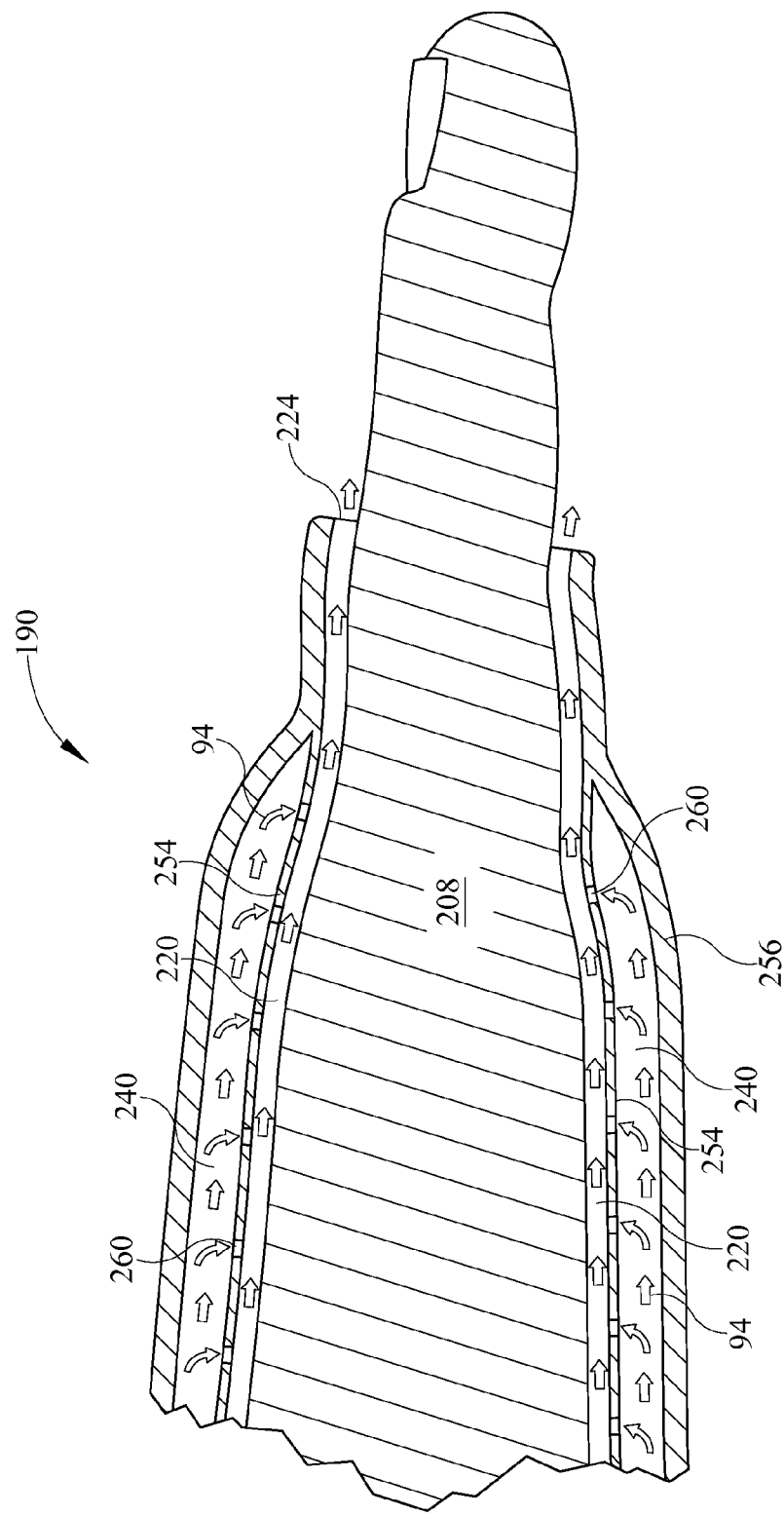

FIGS. 18-19 show a variant of glove 190 in which the flowpath includes both a passage 240 extending through the interior of the glove between inner and outer layers 254, 256 of glove material and a coolant pathway 220 bounded in part by the glove and in part by the wearer's hand. The particular embodiment illustrated has a single large passage 240, rather than individual passages as in FIGS. 15 and 17. The passage includes an array of exhaust openings 260. The annuli 224 formed by the distal ends of the glove fingers and the wearer's fingers define a flowpath or pathway exhaust vent 222. In operation coolant received at glove intake 210 flows through the fluid passage 240, exhausts from the passage to the pathway 220 by way of the passage exhaust openings 260, flows through the pathway 220 along the wearer's skin and vents to the environment by way of the vent annuli 224. Once again, available research suggests that it is probably satisfactory to provide coolant passage and pathway only along the palm side of the glove.

Figure 20:
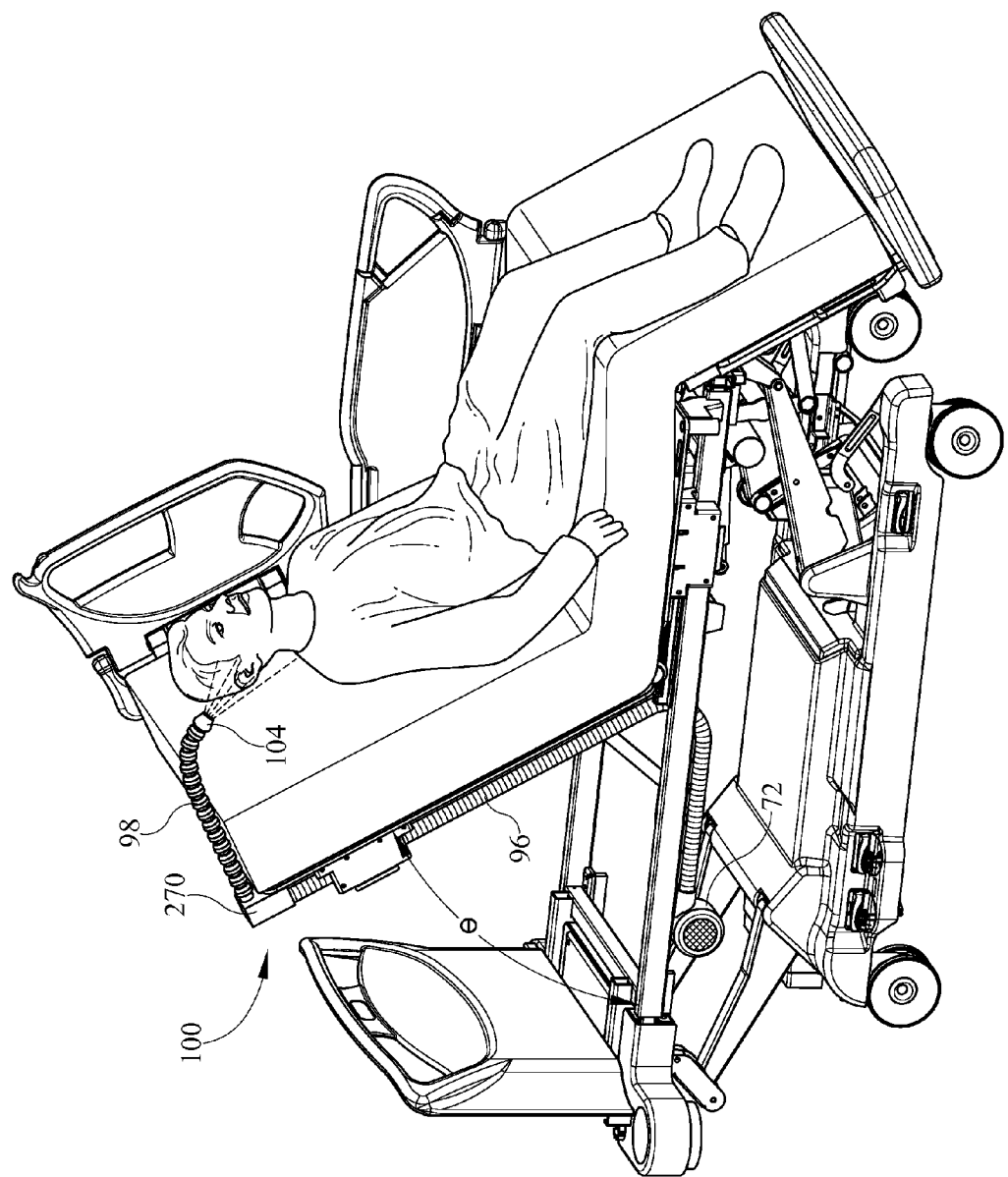
FIG. 20 is a perspective view of another variant of a hospital bed in which the coolant conduit between the blower and the destination location includes a flexible conduit portion non-removably affixed to the bed frame.

FIG. 20 is a perspective view of another variant of a hospital bed and an associated cooling system. The cooling system includes a conduit 100 with a first conduit portion 96 extending from frame mounted blower 72 to a coupler 270. The first conduit portion is non-removably affixed to the bed frame. As used herein, "non-removably affixed" means that conduit is not intended to be routinely and conveniently disengaged from and re-engaged with the frame, as is the case with the securement features 130 of FIGS. 4-5. The first conduit portion is flexible so that it can accommodate changes in the relative angular orientations of the frame parts to which it is affixed, for example changes in angle θ. However the first conduit portion is not necessarily shape stable subsequent to an adjustment of its shape. Conduit 100 also includes a second conduit portion 98 extending from coupler 270 to conduit outlet 104. The second conduit portion 98 is nonpermanently and manually shape adjustable and is shape stable subsequent to adjustment.

Figure 21:
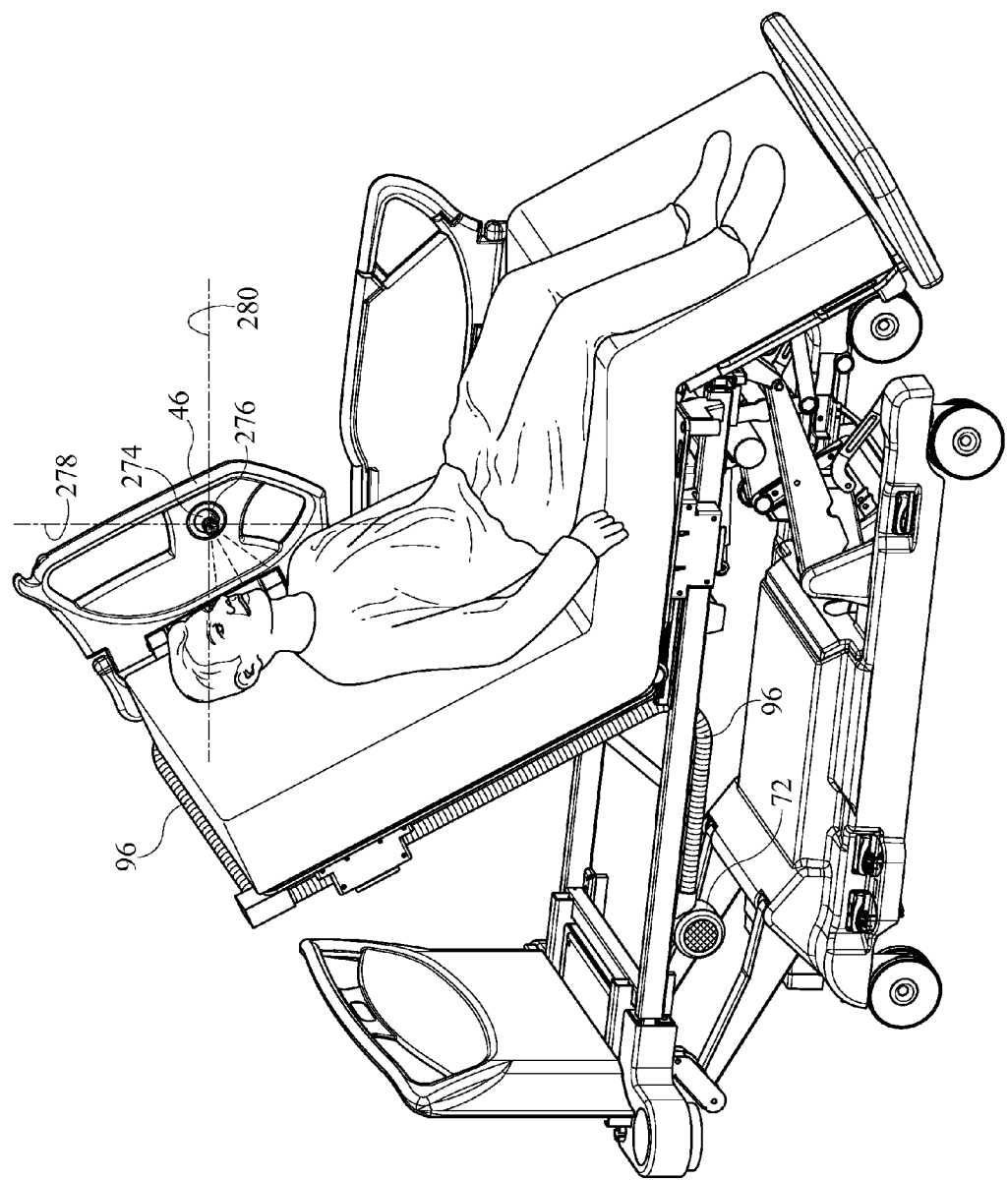
FIG. 21 is a perspective view similar to that of FIG. 20 in which the conduit feeds a nozzle mounted to a siderail.

FIG. 21 is a perspective view similar to that of FIG. 20 in which the conduit feeds a nozzle 274 mounted to a siderail 46. The illustrated nozzle is similar to those used in the passenger cabins of commercial aircraft in which a user can twist a ring 276 on the nozzle to adjust flow rate and can pivot the nozzle about axes 278, 280 to change direction of the coolant stream issuing from the nozzle.

Figure 22:
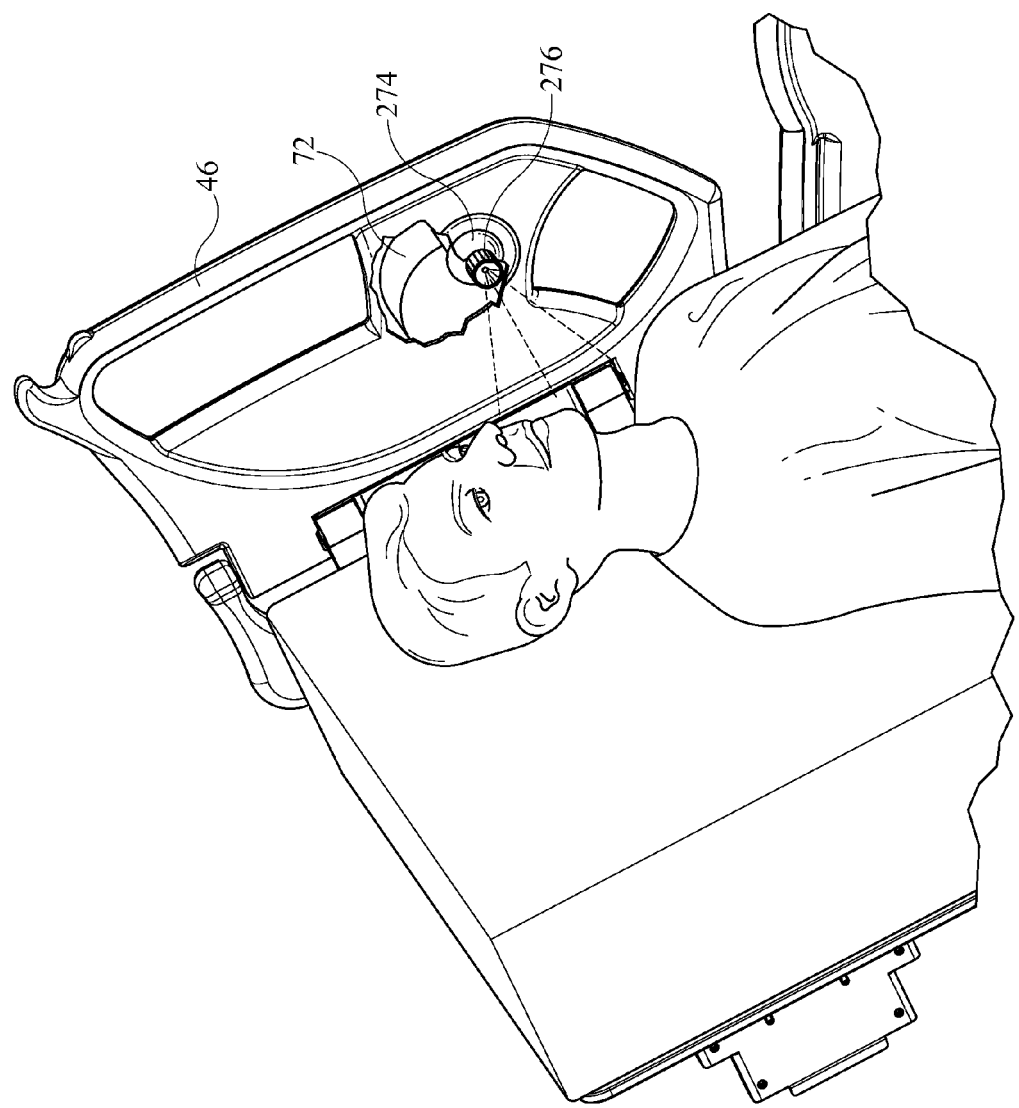
FIG. 22 is a perspective view of another variant of a hospital bed in which the blower and a nozzle similar to that of FIG. 21 are both mounted to a siderail.

FIG. 22 is a perspective view of another variant of a hospital bed in which the blower 72 and a nozzle 274 similar to that of FIG. 21 are both mounted to siderail 46. Alternatively the blower and/or nozzle could be mounted in or on other bed components such as a headboard or footboard.

Although this disclosure refers to specific embodiments, it will be understood by those skilled in the art that various changes in form and detail may be made without departing from the subject matter set forth in the accompanying claims.

We claim:

1. A targeted cooling system for an occupant of an occupant support comprising:
a coolant conduit having an inlet for receiving coolant from a source thereof and an outlet for discharging the coolant to a destination, at least a portion of the conduit being nonpermanently and manually shape adjustable, shape stable subsequent to adjustment, and removably securable to one or both of the occupant support and the occupant wherein the destination is an ambient environment selected to achieve targeted coolant delivery to a localized region of the occupant's body and wherein the localized region is selected from the group consisting of
a) the palms of the occupant's hand, and
b) a trigeminal region of the occupant.

2. A targeted cooling system for an occupant of an occupant support comprising:
a coolant conduit having an inlet for receiving coolant from a source thereof and an outlet for discharging the coolant to a destination, at least a portion of the conduit being nonpermanently and manually shape adjustable, shape stable subsequent to adjustment, and removable securable to one or both of the occupant support and the occupant; and a securement feature associated principally with the conduit for rendering the conduit removably securable to the occupant support or the occupant.

3. A targeted cooling system for an occupant of an occupant support comprising:
a coolant conduit having an inlet for receiving coolant from a source thereof and an outlet for discharging the coolant to a destination, at least a portion of the conduit being nonpermanently and manually shape adjustable, shape stable subsequent to adjustment, and removably securable to one or both of the occupant support and the occupant; and a local blower for providing coolant to the coolant conduit and wherein the local blower is dedicated to the cooling system.

4. A targeted cooling system for an occupant of an occupant support comprising:
a coolant conduit having an inlet for receiving coolant from a source thereof and an outlet for discharging the coolant to a destination, at least a portion of the conduit being nonpermanently and manually shape adjustable, shape stable subsequent to adjustment, and removably securable to one or both of the occupant support and the occupant; and
a local blower for providing coolant to the coolant conduit, wherein the blower includes multiple blower discharge ports, each connectable to a coolant delivery conduit, at least some of the blower discharge ports including means for regulating fluid flow therethrough.

5. A targeted cooling system for an occupant of an occupant support comprising:
a coolant conduit having an inlet for receiving coolant from a source thereof and an outlet for discharging the coolant to a destination, at least a portion of the conduit being nonpermanently and manually shape adjustable, shape stable subsequent to adjustment, and removably securable to one or both of the occupant support and the occupant, the coolant conduit including at least one nonadjustable flow restrictor for limiting mass flow rate of fluid through the conduit.

6. A targeted cooling system for an occupant of an occupant support comprising:
a coolant conduit having an inlet for receiving coolant from a source thereof and an outlet for discharging the coolant to a destination, at least a portion of the conduit being nonpermanently and manually shape adjustable, shape stable subsequent to adjustment, and removably securable to one or both of the occupant support and the occupant, the coolant conduit including means for adjustably regulating coolant flow parameters through the conduit.

7. A targeted cooling system for an occupant of an occupant support having a frame, comprising:
a coolant conduit having a first conduit portion for receiving coolant from a source thereof, the first conduit portion being non-removably affixed to the frame, the conduit also including a second conduit portion having an outlet for discharging the coolant to a destination, the second conduit portion being nonpermanently and manually shape adjustable and shape stable subsequent to adjustment, the first conduit portion being shape adjustable but not shape stable subsequent to adjustment.

8. The cooling system of claim 7 including a discharge nozzle which is at least one of flow rate adjustable and directionally adjustable.

* * * * *